US009018413B2

(12) United States Patent
Hill et al.

(10) Patent No.: US 9,018,413 B2
(45) Date of Patent: Apr. 28, 2015

(54) METHOD FOR THE PRODUCTION OF ALKYLPHOSPHONIC ACIDS, ESTERS, AND SALTS BY OXIDIZING ALKYLPHOSPHONOUS ACIDS, AND USE THEREOF

(75) Inventors: Michael Hill, Cologne (DE); Werner Krause, Huerth (DE); Martin Sicken, Cologne (DE)

(73) Assignee: Clariant Finance (BVI) Limited, Tortola (VG)

( * ) Notice: Subject to any disclaimer, the term of this patent is extended or adjusted under 35 U.S.C. 154(b) by 402 days.

(21) Appl. No.: 13/140,225

(22) PCT Filed: Oct. 6, 2009

(86) PCT No.: PCT/EP2009/007142
§ 371 (c)(1),
(2), (4) Date: Jun. 16, 2011

(87) PCT Pub. No.: WO2010/069418
PCT Pub. Date: Jun. 24, 2010

(65) Prior Publication Data
US 2011/0251314 A1 Oct. 13, 2011

(30) Foreign Application Priority Data
Dec. 18, 2008 (DE) .......................... 10 2008 063 668

(51) Int. Cl.
| C07F 9/22 | (2006.01) |
| C09K 21/12 | (2006.01) |
| C07F 9/38 | (2006.01) |
| C07F 9/40 | (2006.01) |
| C07F 9/48 | (2006.01) |
| C08K 5/5317 | (2006.01) |

(52) U.S. Cl.
CPC .............. *C09K 21/12* (2013.01); *C07F 9/3808* (2013.01); *C07F 9/4006* (2013.01); *C07F 9/4816* (2013.01); *C07F 9/4866* (2013.01); *C08K 5/5317* (2013.01)

(58) Field of Classification Search
None
See application file for complete search history.

(56) References Cited

U.S. PATENT DOCUMENTS

| 3,345,432 A | 10/1967 | Gillham et al. |
| 3,784,638 A | 1/1974 | Lambert |
| 3,875,263 A | 4/1975 | Herwig et al. |
| 3,939,050 A | 2/1976 | Kleiner et al. |
| 3,941,752 A | 3/1976 | Kleiner et al. |
| 3,962,194 A | 6/1976 | Bollert et al. |
| 4,001,352 A | 1/1977 | Kleiner et al. |
| 4,035,343 A | 7/1977 | Bollert et al. |
| 4,069,245 A | 1/1978 | Dursch et al. |
| 4,069,247 A | 1/1978 | Kleiner |
| 4,079,049 A | 3/1978 | Ramsey et al. |
| 4,168,267 A | 9/1979 | Petrillo |
| 4,235,991 A | 11/1980 | Digiacomo |
| 4,337,201 A | 6/1982 | Petrillo |
| 4,374,131 A | 2/1983 | Petrillo |
| 4,381,297 A | 4/1983 | Karanewsky et al. |
| 4,427,665 A | 1/1984 | Karanewsky et al. |
| 4,555,506 A | 11/1985 | Karanewsky et al. |
| 4,594,199 A | 6/1986 | Thottathil et al. |
| 4,602,092 A | 7/1986 | Thottathil et al. |
| 4,634,689 A | 1/1987 | Witkowski et al. |
| 4,670,193 A * | 6/1987 | Thottathil ......................... 562/8 |
| 5,013,863 A | 5/1991 | Baylis et al. |
| 5,153,347 A | 10/1992 | Lloyd |
| 5,190,934 A | 3/1993 | Mickel et al. |
| 5,229,379 A | 7/1993 | Marescaux et al. |
| 5,391,743 A | 2/1995 | Ebitino et al. |
| 5,407,922 A | 4/1995 | Marescaux et al. |
| 5,545,631 A | 8/1996 | Marescaux |
| 5,739,123 A | 4/1998 | Norcini et al. |
| 5,780,534 A | 7/1998 | Kleiner et al. |
| 6,013,707 A | 1/2000 | Kleiner et al. |

(Continued)

FOREIGN PATENT DOCUMENTS

| AT | 243952 | 12/1965 |
| DE | 1494922 | 6/1969 |

(Continued)

OTHER PUBLICATIONS

Montchamp et al. J. Organomet. Chem. 690 (2005), 2388-2406.*

(Continued)

*Primary Examiner* — Susannah Chung
*Assistant Examiner* — Robert T Butcher
(74) *Attorney, Agent, or Firm* — Anthony A. Bisulca

(57) ABSTRACT

The invention relates to a method for producing monocarboxy-functionalized dialkylphosphinic acids, esters, and salts, characterized in that a) a phosphinic acid source (I) is reacted with olefins (IV) in the presence of a catalyst A to obtain an alkylphosphonous acid, the salt or ester (II) thereof, and b) the obtained alkylphosphonous acid, the salt or ester (II) thereof is reacted with an oxidizing agent or with an oxidizing agent and water or with oxygen and water in the presence of a catalyst B to obtain the alkylphosphonic acid derivative (III), wherein $R^1$, $R^2$, $R^3$, $R^4$ are identical or different from each other and independently represent, inter alia, H, $C_1$-$C_{18}$-alkyl, $C_6$-$C_{18}$-aryl, $C_6$-$C_{18}$-aralkyl, $C_6$-$C_{18}$-alkylaryl, X and Y are identical or different from each other and independently represent H, $C_1$-$C_{18}$-alkyl, $C_6$-$C_{18}$-aryl, $C_6$-$C_{18}$-aralkyl, $C_6$-$C_{18}$-alkylaryl, Mg, Ca, Al, Sb, Sn, Ge, Ti, Fe, Zr, Zn, Ce, Bi, Sr, Mn, Cu, Ni, Li, Na, K and/or a protonated nitrogenous base, and catalysts A and B are transition metals and/or transition metal compounds and/or catalyst systems composed of a transition metal and/or a transition metal compound and at least one ligand.

4 Claims, No Drawings

(56) References Cited

U.S. PATENT DOCUMENTS

| | | | |
|---|---|---|---|
| 6,090,968 A | 7/2000 | Horold et al. | |
| 6,214,812 B1 | 4/2001 | Karpeisky | |
| 6,278,012 B1* | 8/2001 | Horold et al. | 558/110 |
| 6,355,832 B1 | 3/2002 | Weferling et al. | |
| 6,384,022 B1 | 5/2002 | Jackson et al. | |
| 6,569,974 B1 | 5/2003 | Sicken et al. | |
| 6,727,335 B2 | 4/2004 | Sicken et al. | |
| 6,855,757 B2 | 2/2005 | Horold et al. | |
| 7,446,140 B2 | 11/2008 | Bauer | |
| 7,473,794 B2 | 1/2009 | Wehner et al. | |
| 7,485,745 B2 | 2/2009 | Maas et al. | |
| 7,749,985 B2 | 7/2010 | Gallop et al. | |
| 7,829,736 B2 | 11/2010 | Wehner et al. | |
| 8,084,518 B2 | 12/2011 | Bauer | |
| 8,097,753 B2 | 1/2012 | Maas et al. | |
| 2002/0187977 A1 | 12/2002 | Pearlman et al. | |
| 2003/0171466 A1 | 9/2003 | Horold et al. | |
| 2003/0216533 A1 | 11/2003 | Sicken et al. | |
| 2005/0187196 A1 | 8/2005 | Madrid et al. | |
| 2006/0084734 A1 | 4/2006 | Bauer et al. | |
| 2006/0194973 A1 | 8/2006 | Gainer et al. | |
| 2006/0264654 A1 | 11/2006 | Wehner et al. | |
| 2007/0029532 A1* | 2/2007 | Hansel et al. | 252/609 |
| 2007/0210288 A1 | 9/2007 | Maas et al. | |
| 2007/0213436 A1* | 9/2007 | Maas et al. | 524/133 |
| 2007/0213563 A1 | 9/2007 | Maas et al. | |
| 2008/0183009 A1 | 7/2008 | Wehner et al. | |
| 2008/0214708 A1 | 9/2008 | Bauer et al. | |
| 2009/0286759 A1 | 11/2009 | Gallop et al. | |
| 2010/0093239 A1 | 4/2010 | Bauer et al. | |
| 2011/0201732 A1 | 8/2011 | Hill et al. | |
| 2011/0201733 A1 | 8/2011 | Hill et al. | |
| 2011/0213052 A1 | 9/2011 | Hill et al. | |
| 2011/0213059 A1 | 9/2011 | Hill et al. | |
| 2011/0213060 A1 | 9/2011 | Hill et al. | |
| 2011/0213061 A1 | 9/2011 | Hill et al. | |
| 2011/0213062 A1 | 9/2011 | Hill et al. | |
| 2011/0213078 A1 | 9/2011 | Hill et al. | |
| 2011/0213079 A1 | 9/2011 | Hill et al. | |
| 2011/0213080 A1 | 9/2011 | Hill et al. | |
| 2011/0224339 A1 | 9/2011 | Hill et al. | |
| 2011/0224340 A1 | 9/2011 | Hill et al. | |
| 2011/0237720 A1 | 9/2011 | Hill et al. | |
| 2011/0237721 A1 | 9/2011 | Hill et al. | |
| 2011/0237722 A1 | 9/2011 | Hill et al. | |
| 2011/0245385 A1 | 10/2011 | Hill et al. | |
| 2011/0245386 A1 | 10/2011 | Hill et al. | |
| 2011/0251310 A1 | 10/2011 | Hill et al. | |
| 2011/0251312 A1 | 10/2011 | Hill et al. | |
| 2011/0251315 A1 | 10/2011 | Hill et al. | |
| 2011/0275744 A1 | 11/2011 | Hill et al. | |
| 2011/0281983 A1 | 11/2011 | Hill et al. | |
| 2012/0064790 A1 | 3/2012 | Bauer et al. | |

FOREIGN PATENT DOCUMENTS

| | | |
|---|---|---|
| DE | 2236036 | 2/1974 |
| DE | 2236037 | 2/1974 |
| DE | 2302523 | 2/1974 |
| DE | 2344332 | 3/1975 |
| DE | 2441878 | 3/1976 |
| DE | 2623775 | 12/1976 |
| DE | 2942781 | 4/1980 |
| DE | 10153780 | 11/2002 |
| DE | 19912920 | 9/2009 |
| EP | 00858391 | 8/1983 |
| EP | 0319482 | 6/1989 |
| EP | 0463560 | 1/1992 |
| EP | 0699708 | 3/1996 |
| EP | 0906915 | 4/1999 |
| EP | 0969008 | 1/2000 |
| EP | 1203770 | 5/2002 |
| EP | 1369422 | 12/2003 |
| EP | 1607400 | 12/2005 |
| EP | 1693403 | 8/2006 |
| EP | 1832594 | 9/2007 |
| EP | 1832595 | 9/2007 |
| EP | 1832596 | 9/2007 |
| EP | 1905776 | 4/2008 |
| GB | 1045684 | 10/1966 |
| JP | 05230085 | 9/1993 |
| WO | WO 99/28327 | 6/1999 |
| WO | WO 01/42252 | 6/2001 |
| WO | WO 0157050 | 8/2001 |
| WO | WO 02/100871 | 12/2002 |
| WO | WO 2005/014604 | 2/2005 |
| WO | WO 2005/032494 | 4/2005 |
| WO | WO 2005/044830 | 5/2005 |
| WO | WO 2007/052169 | 5/2007 |
| WO | WO 2008/033572 | 3/2008 |
| WO | WO 2008/043499 | 4/2008 |

OTHER PUBLICATIONS

US 6,248,921, 06/2001, Weferling et al. (withdrawn).
PCT International Search Report for PCT/EP2009/007145, mailed Jan. 25, 2010.
English Translation of the PCT International Preliminary Report on Patentability PCT/EP2009/007145 mailed Jun. 30, 2011.
English abstract for JP 05230085, Sep. 7, 1993.
Russian Journal of General Chemistry (translation of Zhurnal Obshchei Khimil), 74(6) pp. 864-872; XP002561442 (2004).
PCT International Search Report for PCT/EP2009/007123, mailed Jan. 29, 2010.
English Translation of the PCT International Preliminary Report on Patentability PCT/EP2009/007123 mailed May 19, 2011.
Montchamp; "Recent advances in phosphorus-carbon bond formation: synthesis of H-phosphinic acid derivatives from hypophosphus compounds" Journal of Organometallic Chemistry Elsevier-Sequoua S.A. Lausanne, CH, vol. 690; pp. 2388-2406; XP004877374 (May 16, 2005).
Sylvine Deprele et al. "Palladium-Catalyzed Hydrophosphinylation of Alkenes and Alkynes;" Journal of the American Chemical Society, American Chemical Society, Washington DC, US vol. 124, No. 32 p. 9387, XP002500862 (Jan. 1, 2002).
Bravo-Altamirano et al.: "A Novel Approach to Phosphinic Acids from Hypophosphorus Acid;" Tetrahedron Letters, Elsevier, Amsterdam, NL vol. 48, No. 33, pp. 5755-5759, XP022163552 (Jul. 19, 2007).
Sylvine Deprele et al.: "Environmentally Benign Synthesis of H-Phosphinic Acids Using a Water Tolerant, Recyclable Polymer-Supported Catalyst;" Organic Letters, American Chemical Society, US, vol. 6, No. 21, pp. 3805-3808 XP002500861 (Jan. 1, 2004).
Patrice Ribiere et al: "NiCL2-Catalyzed Hydrophosphinylation;" Journal of Organic Chemistry, American Chemical Society, Easton, US, vol. 70, No. 10, pp. 4064-4072, XP002530191 (Jan. 1, 2005).
Courdray L. et al.: "Allylic Phosphinates via Pd-Catalyzed Allylation of H-Phosphinic Acids with Allylic Alcohols;" Organic letters, vol. 10, No. 6, pp. 1123-1126 XP002561368 (Feb. 21, 2008).
Mastalerz: Synthesis of some ethylene-(P,P'-Dialkyl)-Diphosphic Acids as new Potential Antimetabolites of Succinic Acid; Roczniki Chemii Ann. Soc. Chim. Polonorum, vol. 38 pp. 61-66 XP 009126234 (1964).
Kurdyumova et al.: "Synthesis of Phosphinic Acids from Hypophosphites I Acrylates as an Unsaturated Component;" Russian Journal of General Chemistry (Translation of Zhurnal Obshchei Khimii (1997), 67(12) pp. 1852-1856 (Apr. 25, 1997).
Houben-Weyl, vol. 1211, pp. 258-259 (Apr. 22, 1963).
Houben-Weyl, vol. 1211, p. 306 (Apr. 22, 1963).
English abstract of Khalrullin et al,"Reaction of chlorides of acids of trivalent phosphorus with conjugated systems I. Reaction of ethylphosphonous dichloride with alpha-beta-unstaturated acids" Zh. Obshch. Khimii. 36, pp. 289-296 (1966).
PCT International search report for PCT/EP2009/007124, mailed Feb. 22, 2010.
PCT International Preliminary Report on Patentability for PCT/EP2009/007124, mailed May 19, 2011.

(56) References Cited

OTHER PUBLICATIONS

Piotr Majewski: "A New Method for the Preparation of Bis(1-hydroxyalkyl)-phosphinic Acids;" Synthesis, vol. 6, pp. 555-557, XP002558292 (1987).
Hung Kuei Lin et al.: "Competitive inhibition interfacial catalysis by phospholipase A2: differential interaction of inhibitors with the vesicle interface a controlling factor of inhibitor potency" J. Am. Chem. Soc, vol. 115, No. 10, 1993, pp. 3932-3942 XP009126627 (1993).
Kallinowsky G. et al.: "C13 Nuclear Magnetic Resonance Study of Some Phosphinolipids: Assignments and Conformational Studies;" Magnetic Resonance in Chemistry, vol. 27, No. 7, pp. 647-652 XP00255864 (1989).
PCT International Search Report for PCT/EP2009/007125, mailed Feb. 22, 2010.
English translation of PCT International Preliminary Report on Patentability for PCT/EP2009/007125, mailed May 19, 2011.
PCT International search report for PCT/EP2009/007126, mailed Sep. 2, 2010.
English translation of PCT International Preliminary Report on Patentability for PCT/EP2009/007126, mailed May 19, 2011.
Froestl W. et al.: "Phosphinic Acid Analogues of Gaba. 2. Selective, Orally Acitive Gabab Antagonists," Journal of Medicinal Chemistry, American Chemical Society. Washington, US, vol. 38, No. 17, pp. 3313-3331, XP000999491 (Jan. 1, 1995).
PCT International Preliminary Report on Patentability for PCT/EP2009/007127, mailed Jan. 18, 2010.
English translation of PCT International Preliminary Report on Patentability for PCT/EP2009/007127, mailed May 19, 2011.
PCT International Preliminary Report on Patentability for PCT/EP2009/007128, mailed Jan. 27, 2010.
English translation of PCT International Preliminary Report on Patentability for PCT/EP2009/007128, mailed May 19, 2011.
PCT International Preliminary Report on Patentability for PCT/EP2009/007129, mailed Feb. 22, 2010.
English translation of PCT International Preliminary Report on Patentability for PCT/EP2009/007129, mailed May 19, 2011.
PCT International Preliminary Report on Patentability for PCT/EP2009/007130, mailed Apr. 29, 2010.
English translation of PCT International Preliminary Report on Patentability for PCT/EP2009/007130, mailed May 19, 2011.
Nifant'ev et al.: "Reactions of acetylenes with hypophosphorous aand phosphous acids;" Journal of General Chemistry USSR Consultants Bureau, New York, NY, US vol. 56 No. 4 pp. 680-688 XP002165520 (Sep. 20, 1986).
English Abstract for DE 2344332, Mar. 27, 1975.
Kabachnik et al.: "Synthesis and properties of some ethylenepiphosphoryl compounds," Russian Chemical Bulletin, vol. 23, No. 10 p. 2205 XP002557075 (1974).
Saratovskikh I. et al.: "Phosphorus-containing Aminocarboxylic Acids: XIV, Synthesis of Analogs of [alpha]-Substituted Glutamic Acid" Russian Journal of General Chemistry Nauka/Interperiodica, Mo, vol. 75, No. 7 pp. 1077-1084 XP019301159 (Jul. 1, 2005).
Chemical Abstracts Service, Columbus, Ohio, US: Gareev et al.: "Stereochemistry of a 1,3-dipolar cycloaddition of diazomethane to alpha-substituted vinylphosphoryl compounds containing a chiral phosphorus atom" XP002567581 (1979).
Chemical Abstracts Service, Columbus, Ohio, US: Raevskii et al. "Electron-donor and acceptor functions of physiologically active and model compounds. V. Calculation of the electron-donor function of phosphoryl oxygen" XP002567582 (1984).
Isabelle Abrunhosa Thomas et al.: "Alkylation of H-Phosphinate Esters under Basic Conditions;" Journal of Organic Chemistry, American Chemical Society, Easton,; US, vol. 72, No. 8 pp. 2851-2856 XP002530192 (Jan. 1, 2007).
Catherine Ruflin et al.: "Tetrakis(trimethylsilyl)hypophosphate P2O2(OTMS)4: Synthesis, reactivity and application as flame retardants;" Heteroatom Chemistry, VCH publishers, Defield Beach, FL, US, vol. 18, No. 7 pp. 721-731 XP009118331 (Nov. 6, 2007).

PCT International Search Report for PCT/EP2009/007131, mailed Feb. 8, 2010.
English translation of the PCT International Preliminary Report on Patentability for PCT/EP2009/007131, mailed May 19, 2011.
PCT International Preliminary Report on Patentability for PCT/EP2009/007132, mailed Feb. 15, 2010.
English translation of PCT International Preliminary Report on Patentability for PCT/EP2009/007132, mailed May 19, 2011.
PCT International Preliminary Report on Patentability for PCT/EP2009/007133, mailed Feb. 3, 2010.
English translation of PCT International Preliminary Report on Patentability for PCT/EP2009/007133, mailed May 19, 2011.
Database Beilstein [Online] Beilstein Institute for Organic Chemistry, Frankfurt-Main, DE; XP002561148, retrived from xfire Database accession No. Reaction ID 198358, abstract (1954).
PCT International Preliminary Report on Patentability for PCT/EP2009/007134, mailed Feb. 18, 2010.
English translation of PCT International Preliminary Report on Patentability for PCT/EP2009/007134, mailed May 19, 2011.
PCT International Preliminary Report on Patentability for PCT/EP2009/007135, mailed Mar. 17, 2010.
English translation of PCT International Preliminary Report on Patentability for PCT/EP2009/007135, mailed May 26, 2011.
Bravo-Altamirano et al.: "Palladium-Catalyzed Reaction of Hypophosphorous Compounds with Allenes, Dienes, and Allylic Electrophiles: Methodology for the Synthesis of Allylic H-Phosphinates" J. Org. Chem., vol. 73, No. 6, pp. 2292-2301 XP002567417 (Feb. 15, 2008).
Nadia Valiaeva et al.: "Phosophinic Acid Pseudopeptides Analogous to Glutamyl-gamma-glutamate: Synthesis and Coupling to Pteroyl Azides Leads to Potent Inhibitors of Folypoly-gamma-glutamate Synthetase;" J. Or. Chem., vol. 66, pp. 5146-5154 XP002567418 (2001).
Yamagishi takehiro et al.: "Stereoselective Synthesis of beta-Amino-alpha-hydroxy(allyl)phosphinates and an Application to the Synthesis of a Building Block for Phosphinyl Peptides" Synlett, No. 9, pp. 1471-1474, XP 002567142 (Jan. 1, 2002).
PCT International Search Report for PCT/EP2009/007136, mailed Mar. 22, 2010.
English translation of the PCT International Preliminary Report on Patentability for PCT/EP2009/007136, mailed Jun. 16, 2011.
Database Beilstein [online] Beilstein Institute for Organic Chemistry, Frankfurt-Main, DE; Database accession No. Reaction ID 101395 XP 002567148 (1956).
PCT International Search Report for PCT/EP2009/007137, mailed Mar. 12, 2010.
English translation of the PCT International Preliminary Report on Patentability for PCT/EP2009/007137, mailed Jun. 16, 2011.
Yamagishi et al.: "Diastereoselective synthesis of beta-substituted alpha-hydroxyphosphinates through hydrophosphinylation of alpha-heteroatom-substituted aldehydes;" Tetrahedron, Elsevier Science Publishers, Amsterdam, NL., vol. 59, No. 6 pp. 767-772 XP004404933 (Feb. 3, 2003).
Database Beilstein [online] Beilstein Institute for Organic Chemistry, Frankfurt-Main, DE; Database accession No. Reaction ID 970178 XP 002571550 (1963).
PCT International Search Report for PCT/EP2009/007139, mailed Mar. 22, 2010.
English translation of the PCT International Preliminary Report on Patentability for PCT/EP2009/007139, mailed Jun. 30, 2011.
PCT International Search Report for PCT/EP2009/007140, mailed Mar. 11, 2010.
English translation of the PCT International Preliminary Report on Patentability for PCT/EP2009/007140, mailed Jun. 30, 2011.
PCT International Search Report for PCT/EP2009/008964, mailed Jul. 9, 2010.
English translation of the PCT International Preliminary Report on Patentability for PCT/EP2009/008964, mailed Jun. 30, 2011.
Alonso et al.: "Transition-Metal Catalyzed Addition of Heteroatom-Hydrogen Bonds to Alkynes;" Chem. Rev., pp. 3148-3153 XP002556525 (2004).

(56) References Cited

OTHER PUBLICATIONS

Pudovick et al.: "Free Radical Reaction of Addition of Partial Esters of Phosphorus Acids to Acetylenic Hydrocarbons;" J. Gen. Chem. USSR, vol. 39, No. 5, pp. 986-988 XP009126232 (1969).
Database Beilstein [online] Beilstein Institute for Organic Chemistry, Frankfurt-Main, DE; Database accession No. Reaction BRN 3110535, retrieved from xfire XP002557076 (1967).
Database Beilstein [Online] Beilstein Institute for Organic Chemistry, Frankfurt-Main, DE, Database accession No. Reaction BRN 8075738 XP 002557077 (1997).
PCT International Search Report for PCT/EP2009/007142, mailed Feb. 9, 2010.
English translation of PCT International Preliminary Report on Patentability for PCT/EP2009/007142, mailed Jun. 30, 2011.
English Abstract for SU 314758, Sep. 21, 1971.
Sasse K Ed—Sasse K: "Houben-Weyl Methoden der Organischen Chemie", Organische Phosphor-Verbindungen; [Methoden der Organischen Chemie]. Stuttgart, G. Thieme Verlag DE, XP002500739, pp. 257-259, 261, 294-301 (Jan. 1, 1963).
"1" In: Sasse K Ed—Sasse K: "Houben-Weyl Methoden der Organischen Chemie;" Organische Phosphor-Verbindungen; [Methoden der Organischen Chemie], Stuttgart, G. Thieme Verlag, DE, p. 358, XP002564325 (Jan. 1, 1963).
Regitz:"Houben-Weyl Methoden der Organischen Chemie" Organische Phosphor-Verbindungen; [Methoden der Organischen Chemie], Stuggart, G. Thieme Verlag, DE, pp. 308-309 XP002564334 (Jan. 1, 1982).
Yamagishi et al.: "Lipase-catalyzed kinetic resolution of alpha-hydroxy-H-phosphinates" Tetrahedron Letters, Elsevier, Amsterdam, NL, vol. 45, No. 36, pp. 6713-6716 XP004556626 (Aug. 30, 2004).
Anderson et al.: "Antidiabetic agents: a new class of reversible carnitine palmitoyltrasferase I inhibitors;" J. Med. Chem., vol. 38, No. 18, pp. 3448-3450 XP002564326 (1995).
Karanewsky et al.: "Synthesis of Phosphinic Monoesters from Phosphonous Acids" Tetrahedron Letters, Elsevier, Amsterdam, NL, vol. 27, No. 16, pp. 1751-1754 XP001084930 (Jan. 1, 1986).
Issleib, et al.: "Synthese und Reaktionsverhalten der Athylen-bis-organophosphine;" Chemische Berichte, vol. 101, pp. 2197-2202 XP009126251.
PCT International Search Report for PCT/EP2009/007143, mailed Feb. 17, 2010.
English translation of the PCT International Preliminary Report on Patentability for PCT/EP2009/007143, mailed Jun. 30, 2011.
Regitz: "Houben-Weyl Methoden der Organishcen Chemie" p. 188, (Jan. 1, 1982).
Rezanka et al.: "Synthesis of a Bifunctional Monophosphinate DOTA Derivative Having a Free Carboxylate Group in the Phosphorus Side Chain;" Synthesis, Georg Thieme Verlag, Stuttgart pp. 1431-1435 XP009126087 (Sep. 1, 2008).
Database Beilstein [online] Beilstein Institute for Organic Chemistry, Frankfurt-Main, DE; Database accession No. Reaction ID 938840 XP002557780 (1962).
Diel et al.: "Organische Phosphorverbindungen 84. Herstellung Eigenschaften und Biologische Wirkung von Hydrazino-Methyl-Phosphon-und Phosphinsaeuren und Derivatin;" Phosphorus and Sulfur and the Related Elements, Gordon and Breach—Harwood Academic, CH, vol. 36, pp. 85-98 XP001105809 (Jan. 1, 1998).
Sasse K Ed—Sasse K: "Houben-Weyl Methoden der Organischen Chemie", Organische Phosphor-Verbindungen; [Methoden der Organischen Chemie], Stuttgart, G. Thieme Verlag DE, XP002557781, pp. 228-229 (Jan. 1, 1963).
Kielbasinski et al: "Enzymatic reactions in ionic liquids: lipase-catalysed kinetic resolution of racemic, P-chiral hydroxymethanephosphinates and hydroxmethylphosphine oxides;" Tetrahedron Asymmetry, Pergamon Press Ltd, Oxford, GB, vol. 13, No. 7, pp. 735-738 XP004354866 (May 2, 2002).
Maier: "Organic Phosphorus compounds 91.1 Synthesis and Properties of 1-Amino-2-Arylethylphosphinic and—Phosphinic Acids as well as Phosphine Oxides;" Phosphorus, Sulfur and Silicon and the Related Elements, Gordon and Breach Science Publishers, Amsterdam, GB, vol. 53, No. 1/04 pp. 43-67 XP000671624 (Jan. 1, 1990).
English Translation of Houben-Weyl, vol. 1211, pp. 258-259 (Apr. 22, 1963).
English Translation of Houben-Weyl, vol. 1211, p. 306 (Apr. 22, 1963).
English Translation of Sasse K Ed—Sasse K: "Houben-Weyl Methoden der Organischen Chemie", Organische Phosphor-Verbindungen; [Methoden der Organischen Chemie], Stuttgart, G. Thieme Verlag DE, XP002500739, pp, 257-259, 261, 294-301 (Jan. 1, 1963).
English Translation of "1" In: Sasse K Ed—Sasse K: "Houben-Weyl Methoden der Organischen Chemie;" Organische Phosphor-Verbindungen; [Methoden der Organischen Chemie], Stuttgart, G. Thieme Verlag, DE, p. 358, XP002564325 (Jan. 1, 1963).
English Translation of Regitz: "Houben-Weyl Methoden der Organischen Chemie" Organische Phosphor-Verbindungen; [Methoden der Organischen Chemie], Stuggart, G. Thieme Verlag, DE, pp. 308-309 XP002564334 (Jan. 1, 1982).
English Translation of Issleib, et al.: "Synthese und Reaktionsverhalten der Athylen-bis-organophosphine;" Chemische Berichte, vol. 101, pp. 2197-2202 XP009126251 (1968).
English Translation of Regitz: "Houben-Weyl Methoden der Organishcen Chemie" p. 188, (Jan. 1, 1982).
English Translation of Diel et al.: "Organische Phosphorverbindungen 84. Herstellung Eigenschaften und Biologische Wirkung von Hydrazino-Methyl-Phosphon-und Phosphinsaeuren und Derivatin;" Phosphorus and Sulfur and the Related Elements, Gordon and Breach—Harwood Academic, CH, vol. 36, pp. 85-98 XP001105809 (Jan. 1, 1998).
English Translation of Sasse K Ed—Sasse K: "Houben-Weyl Methoden der Organischen Chemie", Organische Phosphor-Verbindungen; [Methoden der Organischen Chemie], Stuttgart, G. Thieme Verlag DE, XP002557781, pp. 228-229 (Jan. 1, 1963).

* cited by examiner

METHOD FOR THE PRODUCTION OF ALKYLPHOSPHONIC ACIDS, ESTERS, AND SALTS BY OXIDIZING ALKYLPHOSPHONOUS ACIDS, AND USE THEREOF

This invention relates to a method for producing alkylphosphonic acids, esters and salts by means of oxidizing alkylphosphonous acids, and to their use.

Hitherto there are no methods in existence for producing alkylphosphonic acids, esters and salts that are available economically and on a large industrial scale and more particularly enable a high space-time yield to be achieved. Nor are there any methods that are sufficiently effective without unwelcome halogen compounds as starting materials, nor any where the end products are easy to obtain or isolate or else obtainable in a specific and desirable manner under controlled reaction conditions (such as a transesterification for example).

We have found that this object is achieved by a method for producing alkylphosphonic acids, esters and salts, which comprises a) reacting a phosphinic acid source (I)

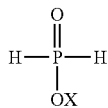

with olefins (IV)

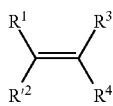

in the presence of a catalyst A to form an alkylphosphonous acid, salt or ester (II)

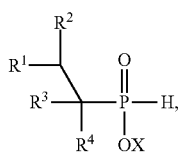

and b) reacting the resulting alkylphosphonous acid, salt or ester (II) with an oxidant or with an oxidant and water or in the presence of a catalyst B with oxygen and water to form the alkylphosphonic acid derivative (III)

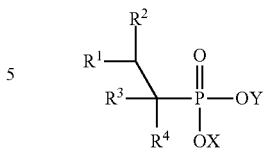

where $R^1$, $R^2$, $R^3$, $R^4$ are identical or different and are each independently H, $C_1$-$C_{18}$-alkyl, $C_6$-$C_{18}$-aryl, $C_6$-$C_{18}$-aralkyl, $C_6$-$C_{18}$-alkylaryl, CN, CHO, $OC(O)CH_2CN$ $CH(OH)C_2H_5$, $CH_2CH(OH)CH_3$, 9-anthracene, 2-pyrrolidone, $(CH_2)_mOH$, $(CH_2)_mNH_2$, $(CH_2)_mNCS$, $(CH_2)_mNC(S)NH_2$, $(CH_2)_mSH$, $(CH_2)_m$S-2-thiazoline, $(CH_2)_mSiMe_3$, $C(O)R^5$, $(CH_2)_mC(O)R^5$, $CH=CHR^5$ and/or $CH=CH-C(O)R^5$ and where $R^5$ is $C_1$-$C_8$-alkyl or $C_6$-$C_{18}$-aryl and m is an integer from 0 to 10 and X and Y are identical or different and are each independently H, $C_1$-$C_{18}$-alkyl, $C_6$-$C_{18}$-aryl, $C_6$-$C_{18}$-aralkyl, $C_6$-$C_{18}$-alkylaryl, $(CH_2)_kOH$, $CH_2$—$CHOH$—$CH_2OH$, $(CH_2)_kO(CH_2)_kH$, $(CH_2)_k$—$CH(OH)$—$(CH_2)_kH$, $(CH_2$—$CH_2O)_kH$, $(CH_2$—$C[CH_3]HO)_kH$, $(CH_2$—$C[CH_3]HO)_k(CH_2$—$CH_2O)_kH$, $(CH_2$—$CH_2O)_k(CH_2$—$C[CH_3]HO)H$, $(CH_2$—$CH_2O)_k$-alkyl, $(CH_2$—$C[CH_3]HO)_k$-alkyl, $(CH_2$—$C[CH_3]HO)_k(CH_2$—$CH_2O)_k$-alkyl, $(CH_2$—$CH_2O)_k(CH_2$—$C[CH_3]HO)$O-alkyl, $(CH_2)_k$—$CH=CH(CH_2)_kH$, $(CH_2)_kNH_2$ and/or $(CH_2)_kN[(CH_2)_kH]_2$, where k is an integer from 0 to 10, and/or Mg, Ca, Al, Sb, Sn, Ge, Ti, Fe, Zr, Zn, Ce, Bi, Sr, Mn, Cu, Ni, Li, Na, K and/or a protonated nitrogen base and the catalysts A and B comprise transition metals and/or transition metal compounds and/or catalyst systems composed of a transition metal and/or transition metal compound and at least one ligand.

Preferably, the alkylphosphonic acid, its salt or ester (III) obtained after step b) is subsequently reacted in a step c) with metal compounds of Mg, Ca, Al, Sb, Sn, Ge, Ti, Fe, Zr, Zn, Ce, Bi, Sr, Mn, Li, Na, K and/or a protonated nitrogen base to form the corresponding alkylphosphonic acid salts (III) of these metals and/or of a nitrogen compound.

Preferably, the alkylphosphonous acid, salt or ester (II) obtained after step a) and/or the alkylphosphonic acid, salt or ester (III) obtained after step b) and/or the particular resulting reaction solution thereof are esterified with an alkylene oxide or an alcohol M-OH and/or M'-OH, and the respectively resulting alkylphosphonous ester (II), and/or akylphosphonic ester (III) are subjected to the further reaction steps b) or c).

Preferably, the groups $C_6$-$C_{18}$-aryl, $C_6$-$C_{18}$-aralkyl and $C_6$-$C_{18}$-alkylaryl are substituted with $SO_3X_2$, $C(O)CH_3$, OH, $CH_2OH$, $CH_3SO_3X_2$, $PO_3X_2$, $NH_2$, $NO_2$, $OCH_3$, SH and/or $OC(O)CH_3$.

Preferably, $R^1$, $R^2$, $R^3$, $R^4$ are identical or different and are each independently H, methyl, ethyl, n-propyl, isopropyl, n-butyl, isobutyl, tert-butyl and/or phenyl.

Preferably, X and Y are identical or different and are each H, Li, Na, K, Ca, Mg, Al, Zn, Ti, Fe, methyl, ethyl, n-propyl, isopropyl, n-butyl, isobutyl, tert-butyl, phenyl, ethylene glycol, propyl glycol, butyl glycol, pentyl glycol, hexyl glycol, allyl and/or glycerol.

Preferably m=1 to 10 and k=2 to 10.

Preferably, the catalyst system A and B is formed by reaction of a transition metal and/or of a transition metal compound and at least one ligand.

Preferably, the transition metals and/or transition metal compounds comprise such from the first, seventh and eighth transition groups.

Preferably, the transition metals and/or transition metal compounds comprise rhodium, nickel, palladium, platinum, ruthenium and/or gold.

The oxidizing agents preferably comprise potassium permanganate, manganese dioxide, chromium trioxide, potassium dichromate, pyridine dichromate, pyridine chlorochromate, Collins reagent, Jones reagent, Corey-Gilman-Ganem reagent, (Dess-Martin)periodinane, o-iodoxybenzoic acid, ruthenium tetroxide, ruthenium dioxide, tetra-n-propyl perruthenate, ruthenium trichloride/sodium periodate, ruthenium dioxide/sodium periodate, chlorine, hypochlorite, peracids and/or peroxo compounds.

Preferably, the alcohol of the general formula M-OH comprises linear or branched, saturated and unsaturated, monohydric organic alcohols having a carbon chain length of $C_1$-$C_{18}$ and the alcohol of the general formula M'-OH comprises linear or branched, saturated and unsaturated polyhydric organic alcohols having a carbon chain length of $C_1$-$C_{18}$.

The present invention also provides for the use of alkylphosphonic acid, esters and salts (III) obtained according to one or more of claims 1 though 3 and 6 as an intermediate for further syntheses, as a binder, as a crosslinker or accelerant to cure epoxy resins, polyurethanes and unsaturated polyester resins, as polymer stabilizers, as crop protection agents, as a therapeutic or additive in therapeutics for humans and animals, as a sequestrant, as a mineral oil additive, as a corrosion control agent, as an acid scavenger, as a flame retardant, in washing and cleaning applications and in electronic applications.

The present invention likewise provides for the use of alkylphosphonic acid salts (III) obtained according to one or more of claims 1 though 3 and 6 as an acid scavenger in a polymer and an amount of 0.0001% to 5% by weight, preferably 0.01% to 2% by weight, more preferably 0.025% to 1% by weight and even more preferably 0.05% to 0.5% by weight based on the particular polymer.

The invention likewise provides for the use of alkylphosphonic acid salts (III) obtained according to one or more of claims 1 though 3 and 6 in mixtures with "classic acid scavengers" as an acid scavenger in a polymer and an amount of the mixture of 0.0001% to 5% by weight, preferably 0.01% to 2% by weight, more preferably 0.025% to 1% by weight and even more preferably 0.05% to 0.5% by weight based on the particular polymer.

The invention likewise provides for the use of flame-retardant thermoplastic or thermoset polymeric molded articles and composites, films, threads and fibers containing 5% to 30% by weight of the alkylphosphonic acids, esters or salts (III) obtained according to one or more of claims 1 though 3 and 6, 5% to 80% by weight of polymer or mixtures thereof, 5% to 40% by weight of additives and 5% to 40% by weight of filler, wherein the sum total of the components is 100% by weight.

All the aforementioned reactions can also be carried out in stages; similarly, the various processing steps can also utilize the respective resulting reaction solutions.

When the alkylphosphonic acid (III) after step b) comprises an ester, an acidic or basic hydrolysis may preferably be carried out in order that the free alkylphosphonic acid or salt may be obtained.

Preferably, the alkylphosphonic acid comprises ethyl-, propyl-, isopropyl-, butyl-, sec-butyl-, isobutyl-, pentyl-, hexyl-, heptyl-, octyl-, decyl-, dodecyl-, hexadecyl-, heptadecyl-, octadecyl- and/or eicosylphosphonic acid.

Preferably, the alkylphosphonic ester comprises a mono- or dipropionic acid, methyl, ethyl; i-propyl; butyl; phenyl; 2-hydroxyethyl, 2-hydroxypropyl, 3-hydroxypropyl, 4-hydroxybutyl and/or 2,3-dihydroxypropyl ester of the aforementioned alkylphosphonic acids or mixtures thereof.

Preferably, the alkylphosphonic salt comprises a sodium, potassium, magnesium, calcium, barium, aluminum(III), cerium(III), titanium(IV) and/or zinc(II) salt of the aforementioned alkylphosphonic acids or esters.

Preferably, the transition metals for catalyst A comprise elements of the seventh and eighth transition groups (a metal of group 7, 8, 9 or 10, in modern nomenclature), for example rhenium, ruthenium, cobalt, rhodium, iridium, nickel, palladium, platinum.

Preference for use as source of the transition metals and transition metal compounds is given to their metal salts. Suitable salts are those of mineral acids containing the anions fluoride, chloride, bromide, iodide, fluorate, chlorate, bromate, iodate, fluorite, chlorite, bromite, iodite, hypofluorite, hypochlorite, hypobromite, hypoiodite, perfluorate, perchlorate, perbromate, periodate, cyanide, cyanate, nitrate, nitride, nitrite, oxide, hydroxide, borate, sulfate, sulfite, sulfide, persulfate, thiosulfate, sulfamate, phosphate, phosphite, hypophosphite, phosphide, carbonate and sulfonate, for example methanesulfonate, chloro-sulfonate, fluorosulfonate, trifluoromethanesulfonate, benzenesulfonate, naphthyl-sulfonate, toluenesulfonate, t-butylsulfonate, 2-hydroxypropane-sulfonate and sulfonated ion exchange resins; and/or organic salts, for example acetyl-acetonates and salts of a carboxylic acid having up to 20 carbon atoms, for example formate, acetate, propionate, butyrate, oxalate, stearate and citrate including halogenated carboxylic acids having up to 20 carbon atoms, for example trifluoroacetate, trichloroacetate.

A further source of the transition metals and transition metal compounds is salts of the transition metals with tetraphenylborate and halogenated tetraphenylborate anions, for example perfluorophenylborate.

Suitable salts similarly include double salts and complex salts consisting of one or more transition metal ions and independently one or more alkali metal, alkaline earth metal, ammonium, organic ammonium, phosphonium and organic phosphonium ions and independently one or more of the abovementioned anions. Examples of suitable double salts are ammonium hexachloropalladate and ammonium tetrachloropalladate.

Preference for use as a source of the transition metals is given to the transition metal as an element and/or a transition metal compound in its zerovalent state.

Preferably, the transition metal salt is used as a metal, or as an alloy with further metals, in which case boron, zirconium, tantalum, tungsten, rhenium, cobalt, iridium, nickel, palladium, platinum and/or gold is preferred here. The transition metal content in the alloy used is preferably 45-99.95% by weight.

Preferably, the transition metal is used in microdisperse form (particle size 0.1 mm-100 µm).

Preferably, the transition metal is used supported on a metal oxide such as, for example, alumina, silica, titanium dioxide, zirconium dioxide, zinc oxide, nickel oxide, vanadium oxide, chromium oxide, magnesium oxide, Celite®, diatomaceous earth, on a metal carbonate such as, for example, barium carbonate, calcium carbonate, strontium carbonate, on a metal sulfate such as, for example, barium sulfate, calcium sulfate, strontium sulfate, on a metal phosphate such as, for example, aluminum phosphate, vanadium phosphate, on a metal carbide such as, for example, silicone carbide, on a metal aluminate such as, for example, calcium aluminate, on a metal silicate such as, for example, aluminum silicate, chalks, zeolites, bentonite, montmorillonite, hectorite, on functionalized silicates, functionalized silica gels such as, for example, SiliaBond®, QuadraSil™, on functionalized polysiloxanes such as, for example, Deloxan®, on a metal nitride, on carbon, activated carbon, mullite, bauxite, antimonite, scheelite, perovskite, hydrotalcite, heteropolyanions, on functionalized and unfunctionalized cellulose, chitosan, keratin, heteropolyanions, on ion exchangers such as, for example, Amberlite™, Amberjet™, Ambersep™, Dowex®, Lewatit®, ScavNet®, on functionalized polymers such as, for example, Chelex®, QuadraPure™, Smopex®, PolyOrgs®, on polymer-bound phosphanes, phosphane oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silica and/or dendrimers.

Suitable sources for the metal salts and/or transition metals likewise preferably include their complex compounds. Complex compounds of the metal salts and/or transition metals are composed of the metal salts/transition metals and one or more complexing agents. Suitable complexing agents include for example olefins, diolefins, nitriles, dinitriles, carbon monoxide, phosphines, diphosphines, phosphites, diphosphites, dibenzylideneacetone, cyclopentadienyl, indenyl or styrene. Suitable complex compounds of the metal salts and/or transition metals may be supported on the abovementioned support materials.

The proportion in which the supported transition metals mentioned are present is preferably in the range from 0.01% to 20% by weight, more preferably from 0.1% to 10% by weight and even more preferably from 0.2% to 5% by weight, based on the total mass of the support material.

Suitable sources for transition metals and transition metal compounds include for example palladium, platinum, nickel, rhodium; palladium platinum, nickel or rhodium, on alumina, on silica, on barium carbonate, on barium sulfate, on calcium carbonate, on strontium carbonate, on carbon, on activated carbon; platinum-palladium-gold alloy, aluminum-nickel alloy, iron-nickel alloy, lanthanide-nickel alloy, zirconium-nickel alloy, platinum-iridium alloy, platinum-rhodium alloy; Raney® nickel, nickel-zinc-iron oxide; palladium(II) chloride, palladium(II) bromide, palladium(II) iodide, palladium(II) fluoride, palladium(II) hydride, palladium(II) oxide, palladium(II) peroxide, palladium(II) cyanide, palladium(II) sulfate, palladium(II) nitrate, palladium(II) phosphide, palladium(II) boride, palladium(II) chromium oxide, palladium(II) cobalt oxide, palladium(II) carbonate hydroxide, palladium(II) cyclohexane butyrate, palladium(II) hydroxide, palladium(II) molybdate, palladium(II) octanoate, palladium(II) oxalate, palladium(II) perchlorate, palladium(II) phthalocyanine, palladium(II) 5,9,14,18,23,27,32,36-octabutoxy-2,3-naphthalocyanine, palladium(II) sulfamate, palladium(II) perchlorate, palladium(II) thiocyanate, palladium(II) bis(2,2,6,6-tetramethyl-3,5-heptanedionate), palladium(II) propionate, palladium(II) acetate, palladium(II) stearate, palladium(II) 2-ethylhexanoate, palladium(II) acetylacetonate, palladium(II) hexafluoroacetylacetonate, palladium(II) tetrafluoroborate, palladium(II) thiosulfate, palladium(II) trifluoroacetate, palladium(II) phthalocyaninetetrasulfonic acid tetrasodium salt, palladium(II) methyl, palladium(II) cyclopentadienyl, palladium(II) methylcyclopentadienyl, palladium(II) ethylcyclopentadienyl, palladium(II) pentamethylcyclopentadienyl, palladium(II) 2,3,7,8,12,13,17,18-octaethyl-21H,23H-porphine, palladium(II) 5,10,15,20-tetraphenyl-21H,23H-porphine, palladium(II) bis(5-[[4-(dimethylamino)phenyl]imino]-8(5H)-quinolinone), palladium(II) 2,11,20,29-tetra-tert-butyl-2,3-naphthalocyanine, palladium(II) 2,9,16,23-tetraphenoxy-29H,31H-phthalocyanine, palladium(II) 5,10,15,20-tetrakis(pentafluorophenyl)-21H,23H-porphine and the 1,4-bis(diphenylphosphine)butane, 1,3-bis(diphenylphosphino)-propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)-imidazolidene)(3-chloropyridyl), 2'-(dimethylamino)-2-biphenylyl, dinorbornylphosphine, 2-(dimethylaminomethyl)ferrocene, allyl, bis(diphenylphosphino)-butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)-phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof; nickel(II) chloride, nickel(II) bromide, nickel(II) iodide, nickel(II) fluoride, nickel(II) hydride, nickel(II) oxide, nickel(II) peroxide, nickel(II) cyanide, nickel(II) sulfate, nickel(II) nitrate, nickel(II) phosphide, nickel(II) boride, nickel(II) chromium oxide, nickel(II) cobalt oxide, nickel(II) carbonate hydroxide, nickel(II) cyclohexane butyrate, nickel(II) hydroxide, nickel(II) molybdate, nickel(II) octanoate, nickel(II) oxalate, nickel(II) perchlorate, nickel(II) phthalocyanine, nickel(II) 5,9,14,18,23,27,32,36-octabutoxy-2,3-naphthalocyanine, nickel(II) sulfamate, nickel(II) perchlorate, nickel(II) thiocyanate, nickel(II) bis(2,2,6,6-tetramethyl-3,5-heptanedionate), nickel(II) propionate, nickel(II) acetate, nickel(II) stearate, nickel(II) 2-ethylhexanoate, nickel(II) acetylacetonate, nickel(II) hexafluoroacetylacetonate, nickel(II) tetrafluoroborate, nickel(II) thiosulfate, nickel(II) trifluoroacetate, nickel(II) phthalocyaninetetrasulfonic acid tetrasodium salt, nickel(II) methyl, nickel(II) cyclopentadienyl, nickel(II) methylcyclopentadienyl, nickel(II) ethylcyclopentadienyl, nickel(II) pentamethylcyclopentadienyl, nickel(II) 2,3,7,8,12,13,17,18-octaethyl-21H,23H-porphine, nickel(II) 5,10,15,20-tetraphenyl-21H,23H-porphine, nickel(II) bis(5-[[4-(dimethylamino)phenyl]imino]-8(5H)-quinolinone), nickel(II) 2,11,20,29-tetra-tert-butyl-2,3-naphthalocyanine, nickel(II) 2,9,16,23-tetraphenoxy-29H,31H-phthalocyanine, nickel(II) 5,10,15,20-tetrakis-(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenyl-sulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylamino-methyl)ferrocene, allyl, bis(diphenylphosphino)butane, (N-succinimidyl)bis-(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof; platinum(II) chloride, platinum(II) bromide, platinum(II) iodide, platinum(II) fluoride, platinum (II) hydride, platinum(II) oxide, platinum(II) peroxide, platinum(II) cyanide, platinum(II) sulfate, platinum(II) nitrate, platinum(II) phosphide, platinum(II) boride, platinum(II) chromium oxide, platinum(II) cobalt oxide, platinum(II) carbonate hydroxide, platinum(II) cyclohexane butyrate, platinum(II) hydroxide, platinum(II) molybdate, platinum(II) octanoate, platinum(II) oxalate, platinum(II) perchlorate, platinum(II) phthalocyanine, platinum(II) 5,9,14,18,23,27,32,36-octabutoxy-2,3-naphthalocyanine, platinum(II) sulfamate, platinum(II) perchlorate, platinum(II) thiocyanate, platinum(II) bis(2,2,6,6-tetramethyl-3,5-heptanedionate), platinum(II) propionate, platinum(II) acetate, platinum(II) stearate, platinum(II) 2-ethylhexanoate, platinum(II) acetylacetonate, platinum(II) hexafluoroacetylacetonate, platinum (II) tetrafluoroborate, platinum(II) thiosulfate, platinum(II) trifluoroacetate, platinum(II) phthalocyaninetetrasulfonic acid tetrasodium salt, platinum(II) methyl, platinum(II) cyclopentadienyl, platinum(II) methylcyclopentadienyl, platinum(II) ethylcyclopentadienyl, platinum(II) pentamethylcyclopentadienyl, platinum(II) 2,3,7,8,12,13,17,18-octaethyl-21H,23H-porphine, platinum(II) 5,10,15,20-tetraphenyl-21H,23H-porphine, platinum(II) bis(5-[[4-(dimethylamino)phenyl]imino]-8(5H)-quinolinone), platinum(II) 2,11,20,29-tetra-tert-butyl-2,3-naphthalocyanine, platinum(II) 2,9,16,23-tetraphenoxy-29H,31H-phthalocyanine, platinum(II) 5,10,15,20-tetrakis(pentafluorophenyl)-21H,23H-porphine and the 1,4-bis-(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenyl-sulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylamino-methyl)ferrocene, allyl, bis(diphenylphosphino)butane, (N-succinimidyl)bis-(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)-imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

rhodium chloride, rhodium bromide, rhodium iodide, rhodium fluoride, rhodium hydride, rhodium oxide, rhodium peroxide, rhodium cyanide, rhodium sulfate, rhodium nitrate, rhodium phosphide, rhodium boride, rhodium chromium oxide, rhodium cobalt oxide, rhodium carbonate hydroxide, rhodium cyclohexane butyrate, rhodium hydroxide, rhodium molybdate, rhodium octanoate, rhodium oxalate, rhodium perchlorate, rhodium phthalocyanine, rhodium 5,9,14,18,23,27,32,36-octabutoxy-2,3-naphthalocyanine, rhodium sulfamate, rhodium perchlorate, rhodium thiocyanate, rhodium bis(2,2,6,6-tetramethyl-3,5-heptanedionate), rhodium propionate, rhodium acetate, rhodium stearate, rhodium 2-ethylhexanoate, rhodium acetylacetonate, rhodium hexafluoroacetylacetonate, rhodium tetrafluoroborate, rhodium thiosulfate, rhodium trifluoroacetate, rhodium phthalocyaninetetrasulfonic acid tetrasodium salt, rhodium methyl, rhodium cyclopentadienyl, rhodium methylcyclopentadienyl, rhodium ethylcyclopentadienyl, rhodium pentamethylcyclopentadienyl, rhodium 2,3,7,8,12,13,17,18-octaethyl-21H,23H-porphine, rhodium 5,10,15,20-tetraphenyl-21H,23H-porphine, rhodium bis(5-[[4-(dimethylamino)phenyl]imino]-8(5H)-quinolinone), rhodium 2,11,20,29-tetra-tert-butyl-2,3-naphthalocyanine, rhodium 2,9,16,23-tetraphenoxy-29H,31H-phthalocyanine, rhodium 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)-imidazolidene)(3-chloropyridyl), 2'-(dimethylamino)-2-biphenylyl, dinorbornylphosphine, 2-(dimethylaminomethyl)ferrocene, allyl, bis(diphenylphosphino)-butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl) imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)-phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

potassium hexachloropalladate(IV), sodium hexachloropalladate(IV), ammonium hexachloropalladate(IV), potassium tetrachloropalladate(II), sodium tetrachloropalladate(II), ammonium tetrachloropalladate(II), bromo(tri-tert-butylphosphine)palladium(I)dimer, (2-methylallyl)palladium (II) chloride dimer, bis(dibenzylideneacetone)palladium(0), tris(dibenzylideneacetone)dipalladium(0), tetrakis(triphenylphosphine)palladium(0), tetrakis(tricyclohexylphosphine)-palladium(0), bis[1,2-bis(diphenylphosphine)ethane]palladium(0), bis(3,5,3',5'-dimethoxydibenzylideneacetone) palladium(0), bis(tri-tert-butylphosphine)-palladium(0), meso-tetraphenyltetrabenzoporphinepalladium, tetrakis(methyldiphenylphosphine)palladium(0), tris(3,3',3''-phophinidyne-tris(benzenesulfonato)-palladium(0) nonasodium salt, 1,3-bis(2,4,6-trimethylphenyl)imidazol-2-ylidene-(1,4-naphthoquinone)palladium(0), 1,3-bis(2,6-diisopropylphenyl)imidazol-2-ylidene(1,4-naphthoquinone)palladium(0) and the chloroform complex thereof; allylnickel(II) chloride dimer, ammoniumnickel(II) sulfate, bis(1,5-cyclooctadiene)nickel(0), bis(triphenylphosphine)dicarbonylnickel(0), tetrakis(triphenylphosphine)nickel(0), tetrakis(triphenyl phosphite)nickel(0), potassium hexafluoronickelate(IV), potassium tetracyanonickelate(II), potassium nickel(IV) paraperiodate, dilithium tetrabromonickelate(II), potassium tetracyanonickelate(II); platinum(IV) chloride, platinum(IV) oxide, platinum(IV) sulfide, potassium hexa-chloroplatinate (IV), sodium hexachloroplatinate(IV), ammonium hexachloro-platinate(IV), potassium tetrachloroplatinate(II), ammonium tetrachloroplatinate(II), potassium tetracyanoplatinate(II), trimethyl(methylcyclopentadienyl)platinum (IV), cis-diammintetrachloroplatinum(IV), potassium trichloro(ethylene)platinate(II), sodium hexahydroxyplatinate(IV), tetraamineplatinum(II) tetrachloroplatinate(II), tetrabutylammonium hexachloroplatinate(IV), ethylenebis (triphenylphosphine)-platinum(0), platinum(0) 1,3-divinyl-1,1,3,3-tetramethyldisiloxane, platinum(0) 2,4,6,8-tetramethyl-2,4,6,8-tetravinylcyclotetrasiloxane, tetrakis (triphenylphosphine)platinum(0), platinum octaethylporphyrine, chloroplatinic acid, carboplatin; chlorobis(ethylene)rhodium dimer, hexarhodium hexadecacarbonyl, chloro(1,5-cyclooctadiene)rhodium dimer, chloro (norbomadiene)rhodium dimer, chloro(1,5-hexadiene) rhodium dimer.

The ligands preferably comprise phosphines of the formula (V)

$$PR^6_3 \qquad (V)$$

where the $R^6$ radicals are each independently hydrogen, straight-chain, branched or cyclic $C_1$-$C_{20}$-alkyl, $C_6$-$C_{20}$-alkylaryl, $C_2$-$C_{20}$-alkenyl, $C_2$-$C_{20}$-alkynyl, $C_1$-$C_{20}$-carboxylate, $C_1$-$C_2$-alkoxy, $C_2$-$C_{20}$-alkenyloxy, $C_2$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkyisulfinyl, silyl and/or their derivatives and/ or phenyl substituted by at least one $R^7$, or naphthyl substituted by at least one $R^7$. $R^7$ in each occurrence is independently hydrogen, fluorine, chlorine, bromine, iodine, $NH_2$, nitro, hydroxyl, cyano, formyl, straight-chain, branched or cyclic $C_1$-$C_{20}$-alkyl, $C_1$-$C_{20}$-alkoxy, $HN(C_1$-$C_{20}$-alkyl), $N(C_1$-$C_{20}$-alkyl)$_2$, —$CO_2$—($C_1$-$C_{20}$-alkyl), —$CON(C_1$-$C_{20}$-alkyl)$_2$, —$OCO(C_1$-$C_{20}$-alkyl), $NHCO(C_1$-$C_{20}$-alkyl), —$SO_3M$, —$SO_2N(R^8)M$, —$CO_2M$, —$PO_3M_2$, —$AsO_3M_2$, —$SiO_2M$, —$C(CF_3)_2OM$ (M=H, Li, Na or K), where $R^8$ is hydrogen, fluorine, chlorine, bromine, iodine, straight-chain, branched or cyclic $C_1$-$C_{20}$-alkyl, $C_2$-$C_{20}$-alkenyl, $C_2$-$C_{20}$-alkynyl, $C_1$-$C_{20}$-carboxylate, $C_1$-$C_{20}$-alkoxy, $C_2$-$C_{20}$-alkenyloxy, $C_2$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or their derivatives, aryl, $C_6$-$C_{20}$-arylalkyl, $C_6$-$C_{20}$-alkylaryl, phenyl and/or biphenyl. Preferably, the $R^6$ groups are all identical.

Suitable phosphines(V) are for example trimethylphosphine, triethylphosphine, tripropylphosphine, triisopropylphosphine, tributylphosphine, triisobutylphosphine, triisopentylphosphine, trihexylphosphine, tricyclohexylphosphine, trioctylphosphine, tridecylphosphine, triphenylphosphine, diphenylmethylphosphine, phenyldimethylphosphine, tri(o-tolyl)phosphine, tri(p-tolyl) phosphine, ethyldiphenylphosphine, dicyclohexylphenylphosphine, 2-pyridyldiphenylphosphine, bis(6-methyl-2-pyridyl)phenylphosphine, tri(p-chlorophenyl)phosphine, tri(p-methoxyphenyl)phosphine, diphenyl(2-sulfonatophenyl)phosphine; potassium, sodium and ammonium salts of diphenyl(3-sulfonatophenyl)phosphine, bis(4,6-dimethyl-3-sulfonatophenyl)(2,4-dimethylphenyl) phosphine, bis(3-sulfonatophenyl)phenylphosphines, tris(4,6-dimethyl-3-sulfonatophenyl)phosphines, tris(2-sulfonatophenyl)phosphines, tris(3-sulfonatophenyl) phosphines; 2-bis(diphenylphosphinoethyl) trimethylammonium iodide, 2'-dicyclohexylphosphino-2,6-dimethoxy-3-sulfonato-1,1'-biphenyl sodium salt, trimethyl phosphite and/or triphenyl phosphite.

The ligands more preferably comprise bidentate ligands of the general formula $$R^6_2M''\text{-}Z\text{-}M''R^6_2 \qquad (VI).$$

In this formula, each M" independently is N, P, As or Sb.
M" is preferably the same in the two occurrences and more preferably is a phosphorus atom.
Each $R^6$ group independently represents the radicals described under formula (V).
The $R^6$ groups are preferably all identical.
Z is preferably a bivalent bridging group which contains at least 1 bridging atom, preferably from 2 to 6 bridging atoms.
Bridging atoms can be selected from carbon, nitrogen, oxygen, silicon and sulfur atoms. Z is preferably an organic bridging group containing at least one carbon atom. Z is preferably an organic bridging group containing 1 to 6 bridging atoms, of which at least two are carbon atoms, and which may be substituted or unsubstituted.

Preferred Z groups are —$CH_2$—, —$CH_2$—$CH_2$—, —$CH_2$—$CH_2$—$CH_2$—, —$CH_2$—$CH(CH_3)$—$CH_2$—, —$CH_2$—$C(CH_3)_2$—$CH_2$—, —$CH_2$—$C(C_2H_5)$—$CH_2$—, —$CH_2$—$Si(CH_3)_2$—$CH_2$—, —$CH_2$—$O$—$CH_2$—, —$CH_2$—$CH_2$—$CH_2$—$CH_2$—, —$CH_2$—$CH(C_2H_5)$—$CH_2$—, —$CH_2$—$CH(n\text{-Pr})$—$CH$ and —$CH_2$—$CH(n\text{-Bu})$—$CH_2$—, substituted or unsubstituted 1,2-phenyl, 1,2-cyclohexyl, 1,1'- or 1,2-ferrocenyl radicals, 2,2'-(1,1'-biphenyl), 4,5-xanthene and/or oxydi-2,1-phenylene radicals.

Examples of suitable bidentate phosphine ligands (VI) are for example 1,2-bis-(dimethylphosphino)ethane, 1,2-bis(diethylphosphino)ethane, 1,2-bis(dipropylphosphino)ethane, 1,2-bis(diisopropylphosphino)ethane, 1,2-bis(dibutylphosphino)ethane, 1,2-bis(di-tert-butylphosphino)ethane, 1,2-bis (dicyclohexylphosphino)ethane, 1,2-bis(diphenylphosphino)ethane; 1,3-bis(dicyclohexylphosphino)propane, 1,3-bis(diisopropylphosphino)propane, 1,3-bis(di-tert-butylphosphino)propane, 1,3-bis(diphenylphosphino) propane; 1,4-bis(diisopropylphosphino)butane, 1,4-bis (diphenylphosphino)butane; 1,5-bis (dicyclohexylphosphino)pentane; 1,2-bis(di-tert-butylphosphino)benzene, 1,2-bis(diphenylphosphino) benzene, 1,2-bis(dicyclohexylphosphino)benzene, 1,2-bis (dicyclopentylphosphino)benzene, 1,3-bis(di-tert-butylphosphino)benzene, 1,3-bis(diphenylphosphino) benzene, 1,3-bis(dicyclohexylphosphino)benzene, 1,3-bis (dicyclopentylphosphino)benzene; 9,9-dimethyl-4,5-bis (diphenylphosphino)xanthene, 9,9-dimethyl-4,5-bis (diphenylphosphino)-2,7-di-tert-butylxanthene, 9,9-dimethyl-4,5-bis(di-tert-butylphosphino)xanthene, 1,1'-bis (diphenylphosphino)ferrocene, 2,2'-bis (diphenylphosphino)-1,1'-binaphthyl, 2,2'-bis(di-p-tolylphosphino)-1,1'-binaphthyl, (oxydi-2,1-phenylene)bis (diphenylphosphine), 2,5-(diisopropylpholano) benzene, 2,3-O-isopropylidene-2,3-dihydroxy-1,4-bis (diphenylphosphino)butane, 2,2'-bis(di-tert-butylphosphino)-1,1'-biphenyl, 2,2'-bis (dicyclohexylphosphino)-1,1'-biphenyl, 2,2'-bis (diphenylphosphino)-1,1'-biphenyl, 2-(di-tert-butylphosphino)-2'-(N,N-dimethylamino)biphenyl, 2-(dicyclohexylphosphino)-2'-(N,N-dimethylamino)biphenyl, 2-(diphenylphosphino)-2'-(N,N-dimethylamino)biphenyl, 2-(diphenylphosphino)ethylamine, 2-[2-(diphenylphosphino)ethyl]pyridine; potassium, sodium and ammonium salts of 1,2-bis(di-4-sulfonatophenyl-phosphino)benzene, (2,2'-bis[[bis(3-sulfonato-phenyl)phosphino]methyl]-4,4',7,7'-tetrasulfonato-1,1'-binapthyl, (2,2'-bis[[bis(3-sulfonatophenyl)phosphino]methyl]-5,5'-tetrasulfonato-1,1-biphenyl, (2,2'-bis[[bis(3-sulfonatophenyl)phosphino]-methyl]-1,1'-binapthyl, (2,2'-bis[[bis(3-sulfonatophenyl) phosphino]methyl]-1,1'-biphenyl, 9,9-dimethyl-4,5-bis (diphenylphosphino)-2,7-sulfonatoxanthene, 9,9-dimethyl-4,5-bis(di-tert-butylphosphino)-2,7-sulfonatoxanthene, 1,2- bis(di-4-sulfonatophenylphosphino)benzene, meso-tetrakis (4-sulfonatophenyl)porphine, meso-tetrakis(2,6-dichloro-3-sulfonatophenyl)porphine, meso-tetrakis(3-sulfonato-mesityl)porphine, tetrakis(4-carboxyphenyl)porphine and 5,11,17,23-sulfonato-25,26,27,28-tetrahydroxycalix[4]arene.

Moreover, the ligands of the formula (V) and (VI) can be attached to a suitable polymer or inorganic substrate by the $R^6$ radicals and/or the bridging group.

The molar transition metal/ligand ratio of the catalyst system is preferably in the range 1:0.01 to 1:100, more preferably in the range from 1:0.05 to 1:10 and more preferably in the range from 1:1 to 1:4.

The reactions in the process stages a), b) and c) preferably take place, if desired, in an atmosphere comprising further gaseous constituents such as nitrogen, oxygen, argon, carbon dioxide for example; the temperature is in the range from −20 to 340° C., more particularly in the range from 20 to 180° C., and total pressure is in the range from 1 to 100 bar.

The products and/or the transition metal and/or the transition metal compound and/or catalyst system and/or the ligand and/or starting materials are optionally isolated after the process stages a), b) and c) by distillation or rectification, by crystallization or precipitation, by filtration or centrifugation, by adsorption or chromatography or other known methods.

According to the present invention, solvents, auxiliaries and any other volatile constituents are removed by distillation, filtration and/or extraction for example.

The reactions in the process stages a), b) and c) are preferably carried out, if desired, in absorption columns, spray towers, bubble columns, stirred tanks, trickle bed reactors, flow tubes, loop reactors and/or kneaders.

Suitable mixing elements include for example anchor, blade, MIG, propeller, impeller and turbine stirrers, cross beaters, disperser disks, hollow (sparging) stirrers, rotor-stator mixers, static mixers, Venturi nozzles and/or mammoth pumps.

The intensity of mixing experienced by the reaction solutions/mixtures preferably corresponds to a rotation Reynolds number in the range from 1 to 1 000 000 and preferably in the range from 100 to 100 000.

It is preferable for an intensive commixing of the respective reactants etc. to be effected by an energy input in the range from 0.080 to 10 kW/m$^3$, preferably 0.30-1.65 kW/m$^3$.

During the reaction, the particular catalyst A or B is preferably homogeneous and/or heterogeneous in action. Therefore, the particular heterogeneous catalyst is effective during the reaction as a suspension or bound to a solid phase.

Preferably, the particular catalyst A or B is generated in situ before the reaction and/or at the start of the reaction and/or during the reaction.

Preferably, the particular reaction takes place in a solvent as a single-phase system in homogeneous or heterogeneous mixture and/or in the gas phase.

When a multi-phase system is used, a phase transfer catalyst may be used in addition.

The reactions of the present invention can be carried out in liquid phase, in the gas phase or else in supercritical phase. The particular catalyst A or B is preferably used in the case of liquids in homogeneous form or as a suspension, while a fixed bed arrangement is advantageous in the case of gas phase or supercritical operation.

Suitable solvents are water, alcohols, e.g. methanol, ethanol, isopropanol, n-propanol, n-butanol, isobutanol, tert-butanol, n-amyl alcohol, isoamyl alcohol, tert-amyl alcohol, n-hexanol, n-octanol, isooctanol, n-tridecanol, benzyl alcohol, etc. Preference is further given to glycols, e.g. ethylene glycol, 1,2-propanediol, 1,3-propanediol, 1,3-butanediol, 1,4-butanediol, diethylene glycol etc.; aliphatic hydrocarbons, such as pentane, hexane, heptane, octane, and petroleum ether, naphtha, kerosene, petroleum, paraffin oil, etc.; aromatic hydrocarbons, such as benzene, toluene, xylene, mesitylene, ethylbenzene, diethylbenzene, etc.; halogenated hydrocarbons, such as methylene chloride, chloroform, 1,2-dichloro-ethane, chlorobenzene, carbon tetrachloride, tetrabromoethylene, etc.; alicyclic hydrocarbons, such as cyclopentane, cyclohexane, and methylcyclohexane, etc.; ethers, such as anisole (methyl phenyl ether), tert-butyl methyl ether, dibenzyl ether, diethyl ether, dioxane, diphenyl ether, methyl vinyl ether, tetrahydrofuran, triisopropyl ether etc.; glycol ethers, such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether etc.; ketones, such as acetone, diisobutyl ketone, methyl n-propyl ketone; methyl ethyl ketone, methyl isobutyl ketone etc.; esters, such as methyl formate, methyl acetate, ethyl acetate, n-propyl acetate, and n-butyl acetate, etc.; carboxylic acids, such as formic acid, acetic acid, propionic acid, butyric acid, etc. One or more of these compounds can be used, alone or in combination.

Suitable solvents also encompass the phosphinic acid sources and olefins used. These have advantages in the form of higher space-time yield.

It is preferable that the reaction be carried out under the autogenous vapor pressure of the olefin and/or of the solvent.

Preferably, $R^1$, $R^2$, $R^3$ and $R^4$ of olefin (IV) are the same or different and each is independently H, methyl, ethyl, n-propyl, isopropyl, n-butyl, isobutyl, tert-butyl and/or phenyl.

Preference is also given to using functionalized olefins such as allyl isothiocyanate, allyl methacrylate, 2-allylphenol, N-allylthiourea, 2-(allylthio)-2-thiazoline, allyltrimethylsillane, allyl acetate, allyl acetoacetate, allyl alcohol, allylamine, allylbenzene, allyl cyanide, allyl cyanoacetate, allylanisole, trans-2-pentenal, cis-2-pentenenitrile, 1-penten-3-ol, 4-penten-1-ol, 4-penten-2-ol, trans-2-hexenal, trans-2-hexen-1-ol, cis-3-hexen-1-ol, 5-hexen-1-ol, styrene, -methylstyrene, 4-methylstyrene, vinyl acetate, 9-vinylanthracene, 2-vinylpyridine, 4-vinylpyridine or 1-vinyl-2-pyrrolidone.

The partial pressure of the olefin during the reaction is preferably 0.01-100 bar and more preferably 0.1-10 bar.

The phosphinic acid/olefin molar ratio for the reaction is preferably in the range from 1:10 000 to 1:0.001 and more preferably in the range from 1:30 to 1:0.01.

The phosphinic acid/catalyst molar ratio for the reaction is preferably in the range from 1:1 to 1:0.00000001 and more preferably in the range from 1:0.01 to 1:0.000001.

The phosphinic acid/solvent molar ratio for the reaction is preferably in the range from 1:10 000 to 1:0 and more preferably in the range from 1:50 to 1:1.

One method the present invention provides for producing compounds of the formula (II) comprises reacting a phosphinic acid source with olefins in the presence of a catalyst and freeing the product (II) (alkylphosphonous acid, salts or esters) of catalyst, transition metal or transition metal compound as the case may be, ligand, complexing agent, salts and by-products.

The present invention provides that the catalyst, the catalyst system, the transition metal and/or the transition metal compound are separated off by adding an auxiliary 1 and removing the catalyst, the catalyst system, the transition metal and/or the transition metal compound by extraction and/or filtration.

The present invention provides that the ligand and/or complexing agent is separated off by extraction with auxiliary 2 and/or distillation with auxiliary 2.

Auxiliary 1 is preferably water and/or at least one member of the group of metal scavengers. Preferred metal scavengers are metal oxides, such as aluminum oxide, silicon dioxide, titanium dioxide, zirconium dioxide, zinc oxide, nickel oxide, vanadium oxide, chromium oxide, magnesium oxide, Celite®, kieselguhr, metal carbonates, such as barium carbonate, calcium carbonate, strontium carbonate, metal sulfates, such as barium sulfate, calcium sulfate, strontium sulfate, metal phosphates, such as aluminum phosphate, vanadium phosphate, metal carbides, such as silicone carbide, metal aluminates, such as calcium aluminate, metal silicates, such as aluminum silicate, chalks, zeolites, bentonite, montmorillonite, hectorite, functionalized silicates, functionalized silica gels, such as SiliaBond®, QuadraSil™, functionalized polysiloxanes, such as Deloxan®, metal nitrides, carbon, activated carbon, mullite, bauxite, antimonite, scheelite, perovskite, hydrotalcite, functionalized and unfunctionalized cellulose, chitosan, keratin, heteropolyanions, ion exchangers, such as Amberlite™, Amberjet™, Ambersep™, Dowex®, Lewatit®, ScavNet®, functionalized polymers, such as Chelex®, QuadraPure™, Smopex®, Poly-Orgs®, polymer-bound phosphanes, phosphane oxides, phosphinates, phosphonates, phosphates, amines, ammonium salts, amides, thioamides, urea, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silicon dioxide, and/or dendrimers.

It is preferable that the amounts added of auxiliary 1 correspond to 0.1-40% by weight loading of the metal on auxiliary 1.

It is preferable that auxiliary 1 be used at temperatures of from 20 to 90° C.

It is preferable that the residence time of auxiliary 1 be from 0.5 to 360 minutes.

Auxiliaries 2 are preferably the aforementioned solvents of the present invention as are preferably used in process stage a).

The esterification of the alkylphosphonic acid (III) or of the alkylphosphonous acid derivatives (II) and also of the phosphinic acid source (I) to form the corresponding esters can be achieved for example by reaction with higher-boiling alcohols by removing the resultant water by azeotropic distillation, or by reaction with epoxides (alkylene oxides).

Preferably, following step a), the alkylphosphonous acid (II) is directly esterified with an alcohol of the general formula M-OH and/or M'-OH or by reaction with alkylene oxides, as indicated hereinbelow.

M-OH preferably comprises primary, secondary or tertiary alcohols having a carbon chain length of $C_1$-$C_{18}$. Particular preference is given to methanol, ethanol, propanol, isopropanol, n-butanol, 2-butanol, tert-butanol, amyl alcohol and/or hexanol.

M'-OH preferably comprises ethylene glycol, 1,2-propylene glycol, 1,3-propylene glycol, 1,4-butanediol, 2,2-dimethylpropane-1,3-diol, neopentyl glycol, 1,6-hexane-diol, 1,4-cyclohexanedimethanol, glycerol, trishydroxymethylethane, trishydroxymethylpropane, pentaerythritol, sorbitol, mannitol, α-naphthol, polyethylene glycols, polypropylene glycols and/or EO-PO block polymers.

Also useful as M-OH and M'-OH are mono- or polyhydric unsaturated alcohols having a carbon chain length of $C_{1-18}$, for example n-but-2-en-1-ol, 1,4-butenediol and allyl alcohol.

Also useful as M-OH and M'-OH are reaction products of monohydric alcohols with one or more molecules of alkylene oxides, more preferably ethylene oxide and 1,2-propylene oxide. Preference is given to 2-methoxyethanol, 2-ethoxyethanol, 2-n-butoxyethanol, 2-(2'-ethylhexyloxy)ethanol, 2-n-dodecoxyethanol, methyl diglycol, ethyl diglycol, isopropyl diglycol, fatty alcohol polyglycol ethers and aryl polyglycol ethers.

M-OH and M'-OH are also preferably reaction products of polyhydric alcohols with one or more molecules of alkylene oxide, more particularly diglycol and triglycol and also adducts of 1 to 6 molecules of ethylene oxide or propylene oxide onto glycerol, trishydroxymethylpropane or pentaerythritol.

Useful M-OH and M'-OH further include reaction products of water with one or more molecules of alkylene oxide. Preference is given to polyethylene glycols and poly-1,2-propylene glycols of various molecular sizes having an average molecular weight of 100-1000 g/mol and more preferably of 150-350 g/mol.

Preference for use as M-OH and M'-OH is also given to reaction products of ethylene oxide with poly-1,2-propylene glycols or fatty alcohol propylene glycols; similarly reaction products of 1,2-propylene oxide with polyethylene glycols or fatty alcohol ethoxylates. Preference is given to such reaction products with an average molecular weight of 100-1000 g/mol, more preferably of 150-450 g/mol.

Also useful as M-OH and M'-OH are reaction products of alkylene oxides with ammonia, primary or secondary amines, hydrogen sulfide, mercaptans, oxygen acids of phosphorus and $C_2$-$C_6$ dicarboxylic acids. Suitable reaction products of ethylene oxide with nitrogen compounds are triethanolamine, methyldiethanol-amine, n-butyldiethanolamine, n-dodecyldiethanolamine, dimethylethanolamine, n-butylmethylethanolamine, di-n-butylethanolamine, n-dodecylmethylethanol-amine, tetrahydroxyethylethylenediamine or pentahydroxyethyldiethylenetriamine.

Preferred alkylene oxides are ethylene oxide, 1,2-propylene oxide, 1,2-epoxy-butane, 1,2-epoxyethylbenzene, (2,3-epoxypropyl)benzene, 2,3-epoxy-1-propanol and 3,4-epoxy-1-butene.

Suitable solvents are the solvents mentioned in process step a) and also the M-OH and M'-OH alcohols and alkylene oxides used. These offer advantages in the form of a higher space-time yield.

The reaction is preferably carried out under the autogenous vapor pressure of the employed alcohol M-OH and M'-OH and alkylene oxide and/or of the solvent.

Preferably, the reaction is carried out at a partial pressure of the employed alcohol M-OH and M'-OH and alkylene oxide of 0.01-100 bar, more preferably at a partial pressure of the olefin of 0.1-10 bar.

The reaction is preferably carried out at a temperature in the range from −20 to 340° C. and is more preferably carried out at a temperature in the range from 20 to 180° C.

The reaction is preferably carried out at a total pressure in the range from 1 to 100 bar.

The reaction is preferably carried out in a molar ratio for the alcohol or alkylene oxide component to the phosphinic acid source (I) or alkylphosphonous acid (II) or alkylphosphonic acid (III) ranging from 10 000:1 to 0.001:1 and more preferably from 1000:1 to 0.01:1.

The reaction is preferably carried out in a molar ratio for the phosphinic acid source (I) or alkylphosphonous acid (II) or alkylphosphonic acid (III) to the solvent ranging from 1:10 000 to 1:0 and more preferably in a phosphinic acid/solvent molar ratio ranging from 1:50 to 1:1.

The conversion to alkylphosphonic acid, salts and esters (III) which is described in step b) is achieved through selective oxidation of the alkylphosphonous acid, salts and esters (II) by means of an oxidizing agent, an oxidizing agent and water or by means of oxygen and water in the presence of a catalyst B.

Preferred oxidizing agents and/or oxygen formers are potassium permanganate, manganese dioxide, chromium trioxide, potassium dichromate, pyridine dichromate, pyridine chlorochromate, Collins reagent, Jones reagent, Corey-Gilman-Ganem reagent, (Dess-Martin)periodinane, o-iodoxybenzoic acid, ruthenium tetroxide, ruthenium dioxide, tetra-n-propyl perruthenate, ruthenium trichloride/sodium periodate, ruthenium dioxide/sodium periodate, chlorine, hypochlorite, peracids, for example hydrogen peroxide, performic acid and peracetic acid, nitroxyl free radicals, for example 2,2,6,6-tetramethylpiperidine N-oxide (TEMPO).

In addition to the abovementioned oxidizing agents and/or oxygen formers it is also possible to use peroxo compounds such as peroxomonosulfuric acid, potassium monopersulfate (potassium peroxomonosulfate), Caroat™, Oxone™, peroxodisulfuric acid, potassium persulfate (potassium peroxodisulfate), sodium persulfate (sodium peroxodisulfate), ammonium persulfate (ammonium peroxodisulfate).

Particularly preferred oxidizing agents and/or oxygen formers are compounds capable of forming peroxides in the solvent system, such as sodium peroxide, sodium peroxide hydrates, sodium peroxide diperoxohydrate, sodium peroxide diperoxohydrates, lithium peroxide, lithium peroxide hydrates, calcium peroxide, strontium peroxide, barium peroxide, magnesium peroxide, zinc peroxide, potassium hyperoxide, potassium hyperoxide hydrates, sodium peroxoborate, sodium peroxoborate hydrates, potassium peroxoborate peroxohydrate, magnesium peroxoborate, calcium peroxoborate, barium peroxoborate, strontium peroxoborate, potassium peroxoborate, peroxomonophosphoric acid, peroxodiphosphoric acid, potassium peroxodiphosphate, ammonium peroxodiphosphate, potassium ammonium peroxodiphosphates, sodium carbonate peroxohydrate, urea peroxohydrate, ammonium oxalate peroxide, barium peroxide peroxohydrate, barium peroxide peroxohydrate, calcium hydrogen peroxides, calcium peroxide peroxohydrate, ammonium triphosphate diperoxophosphate hydrate, potassium fluoride peroxohydrate, potassium fluoride triperoxohydrate, potassium fluoride diperoxohydrate, sodium pyrophosphate diperoxohydrate, sodium pyrophosphate diperoxohydrate octahydrate, potassium acetate peroxohydrate, sodium phosphate peroxohydrate, sodium silicate peroxohydrate.

Preferred oxidizing agents and/or oxygen formers are hydrogen peroxide, performic acid, peracetic acid, benzoyl peroxide, di-t-butyl peroxide, dicumyl peroxide, 2,4-di-chlorobenzoyl peroxide, decanoyl peroxide, lauryl peroxide, cumene hydroperoxide, pinene hydroperoxide, p-menthane hydroperoxide, t-butyl hydroperoxide, acetylacetone peroxide, methyl ethyl ketone peroxide, succinic acid peroxide, dicetyl peroxydicarbonate, t-butyl peroxyacetate, t-butylperoxy-maleic acid, t-butyl peroxybenzoate, acetyl cyclohexylsulfonyl peroxide.

The reaction is preferably carried out in a dialkylphosphinic acid/oxidizing agent molar ratio in the range from 1:10 to 1:0.1, and more preferably in a dialkylphosphinic acid/oxidizing agent molar ratio in the range from 1:2 to 1:0.25.

The catalyst B as used for process step b) for the reaction of the alkylphosphonous acid derivative (II) with oxygen and water to form the end product, the alkyiphosphonic acid derivative (III) may preferably be the catalyst A.

The transition metals for catalyst C preferably additionally comprise elements from the first transition group such as, for example, gold.

In addition to the sources of transition metals and transition metal compounds that were listed under catalyst A it is also possible to use the following transition metals and transition metal compounds:

gold, colloidal gold, ruthenium, ruthenium on charcoal, on carbon, on alumina, platinum-palladium-gold alloy, gold-nickel alloy, gold-germanium alloy, gold-platinum alloy, gold-palladium alloy, gold-beryllium alloy, platinum-ruthenium alloy, palladium-ruthenium alloy, gold(I) and/or gold (III), ruthenium(II) and/or ruthenium(III) and/or ruthenium (IV) chloride, bromide, iodide, oxide, cyanide, potassium cyanide, sodium cyanide, sulfide, sulfate, hydride, nitrosylchloride, nitrosylnitrate, bathophenanthroline disulfonate sodium salt, thiosulfate, perchlorate, cyclopentadienyl, ethylcyclopentadienyl, pentamethylcyclopentadienyl, indenyl, 2-methylallyl, propionate, acetate, acetylacetonate, hexafluoroacetylacetonate, tetrafluoroborate, potassium thiocyanate, sodium thiocyanate, trifluoroacetate, bis(trifluoromethanesulfonyl)imidate, hexafluoroantimonate, 2-pyridinecarboxylate and their 1,4-bis(diphenylphosphine)butane, 1,3-bis(diphenylphosphino)propane, 2-(2'-di-tert-butylphosphine)biphenyl, acetonitrile, benzonitrile, dinorbornylphosphine, 1,4-bis(diphenylphosphino)butane, dimethylphenylphosphine, methyldiphenylphosphine, triphenylphosphine, tri-o-tolylphosphine, tricyclohexylphosphine, tributylphosphine, tri-tert-butylphosphine, trimethylphosphine, triethylphosphine, 2,2'-bis(diphenylphosphino)-1,1'-binaphthyl, 1,3-bis(mesityl)imidazol-2-ylidene, 1,1'-bis(diphenylphosphino)ferrocene, (1,1'-biphenyl-2-yl) di-tert-butylphosphine, 1,3-bis(2,6-diisopropylphenyl)imidazol-2-ylidene, 2-dicyclohexyl(2',4',6'-triisopropylbiphenyl)phosphine, dimethyl sulfide, tris(2,4-di-tert-butylphenyl) phosphite, tris(para-trifluoromethylphenyl)phosphine, bis(diphenylphosphino)methane, 1,2-bis(diphenylphosphino) ethane, N-methylimidazole, 1,10-phenanthroline, 4,7-diphenyl-1,10-phenanthroline, 1,5-cyclooctadiene, 1,3,5-cyclooctatriene, naphthalene, p-cymene, 3-methyl-2-butenylidene, benzylidene, pyridine, 2,3,7,8,12,13,17,18-octaethyl-21H,23H-porphine, 5,10,15,20-tetraphenyl-21H, 23H-porphine, N,N,N',N'-tetramethylethylenediamine, tri-o-tolylphosphine, 2,2'-bis(diphenylphosphino)-1,1'-binaphthyl, 1,1'-bis(diphenylphosphino)ferrocene, 2,2'-bipyridine, (bicyclo[2.2.1]hepta-2,5-diene), bis(di-tert-butyl (4-dimethylaminophenyl)phosphine), 2-(di-tert-butylphosphino)ethylamine, (2-(diphenylphosphino) ethylamine, 1,3-bis(2,4,6-trimethylphenyl)-2-imidazolidinylidene, 1,2-diaminocyclohexane, pyridine, carbonyl, ethylenediamine, amine complexes; potassium dicyanoaurate(I), sodium tetrachloroaurate(III), potassium gold(III) chloride, sodium aurothiomalate, tris(triphenylphosphinegold)-oxonium tetrafluoroborate, hydrogen tetrabromoaurate(III); ammonium hexachlororuthenate(IV), potassium aquapentachlororuthenate(III), (1,5-cyclooctadiene)(1,3,5-cyclooctatriene)ruthenium, triruthenium dodecacarbonyl, Grubbs catalyst.

The proportion of catalyst B based on the alkylphosphonous acid (II) is preferably in the range from 0.00001 to 20 mol % and more preferably in the range from 0.0001 to 10 mol %.

The reaction is preferably carried out in a phosphinic acid/solvent molar ratio of 1:10 000 to 1:0 and more preferably in a phosphinic acid/solvent molar ratio of 1:50 to 1:1.

The oxidation temperature is preferably in the range from 30 to 120° C. and more preferably in the range from 50 to 90° C.

The reaction time is preferably in the range from 0.1 to 20 hours.

The reaction is preferably carried out at a total pressure of 1 to 100 bar.

Suitable solvents for process stage b) are those used above in process stage a).

The reaction is preferably carried out at an oxygen partial pressure of 0.01-100 bar and preferably at 0.1-10 bar.

The oxidation of the present invention can be carried out in liquid phase, in the gas phase or else in supercritical phase. In this case the catalyst is used in the case of liquids, preferably in homogeneous form or as a suspension, while a fixed bed arrangement is of advantage in the case of gas phase or supercritical operation.

Preferably, the pH of the reaction solution is maintained in a range of pH 6 to 12 and more preferably in a range of pH 6 to 9 by addition of alkali metal and/or alkaline earth metal compounds.

Preferred alkali and/or alkaline earth metals are lithium, sodium, potassium, magnesium, calcium, barium.

Preferred alkali and/or alkaline earth metal compounds are their oxides, hydroxides, carbonates and carboxylates.

Preferred alkali and/or alkaline earth metal compounds are lithium hydroxide, lithium hydride, sodium hydroxide, sodium hydride, potassium hydroxide.

Preferably, the oxygen is used as pure oxygen or alternatively an oxygen-containing mixture, for example air or oxygen-enriched air.

Preferably, the oxygen is used in the form of oxygen formers such as hydrogen peroxide for example.

The ratio of oxygen to phosphorus-containing compound (II) is preferably in the range from 1:1 to 1500:1.

The alkylphosphonic acid, ester or salt (III) can thereafter be converted into further metal salts.

The metal compounds which are used in process stage c) preferably comprise compounds of the metals Mg, Ca, Ba, Al, Sb, Sn, Ge, Ti, Fe, Zr, Zn, Ce, Bi, Sr, Mn, Li, Na, K, more preferably Li, Na, K, Mg, Ca, Al, Ti, Zn, Fe.

Suitable solvents for process stage c) are those used above in process stage a).

The reaction of process stage c) is preferably carried out in an aqueous medium.

Process stage c) preferably comprises reacting the alkylphosphonic acids, esters and/or alkali metal salts (III) obtained after process stage b) with metal compounds of Li, Na, K, Mg, Ca, Al, Ti, Zn or Fe to form the alkylphosphonic acid salts (III) of these metals.

The reaction is carried out in a molar ratio of alkylphosphonic acid, ester or salt (III) to metal in the range from 8:1 to 1:3 (for tetravalent metal ions or metals having a stable tetravalent oxidation state), from 6:1 to 1:3 (for trivalent metal ions or metals having a stable trivalent oxidation state), from 4:1 to 1:3 (for divalent metal ions or metals having a stable divalent oxidation state) and from 3:1 to 1:4 (for monovalent metal ions or metals having a stable monovalent oxidation state).

Preferably, alkylphosphonic acid, ester or salt (III) obtained in process stage b) is converted into the corresponding alkylphosphonic acid and the latter is reacted in process stage c) with metal compounds of Li, Na, K, Mg, Ca, Al, Ti, Zn or Fe to form the alkylphosphonic acid salts (III) of these metals.

Preferably, alkylphosphonic acid/ester obtained in process stage b) is converted to an alkylphosphonic acid alkali metal salt and the latter is reacted in process stage c) with metal compounds of Li, Na, K, Mg, Ca, Al, Ti, Zn or Fe to form the alkylphosphonic acid salts (III) of these metals.

The metal compounds of Li, Na, K, Mg, Ca, Al, Ti, Zn or Fe for process stage c) preferably comprise metals, metal oxides, hydroxides, oxide hydroxides, borates, carbonates, hydroxocarbonates, hydroxocarbonate hydrates, mixed metal hydroxocarbonates, mixed metal hydroxocarbonate hydrates, phosphates, sulfates, sulfate hydrates, hydroxosulfate hydrates, mixed metal hydroxosulfate hydrates, oxysulfates, acetates, nitrates, fluorides, fluoride hydrates, chlorides, chloride hydrates, oxychlorides, bromides, iodides, iodide hydrates, carboxylic acid derivatives and/or alkoxides.

The reaction in process stage c) of alkylphosphonic acids and/or salts with metal compounds of Li, Na, K, Mg, Ca, Al, Ti, Zn or Fe to form the alkylphosphonic acid salts of these metals is preferably carried out at a solids content of the alkylphosphonic acid salts of these metals in the range from 0.1% to 95% by weight, preferably 5% to 70% by weight.

The reaction in process stage c) is preferably carried out at a temperature of 20 to 250° C., preferably at a temperature of 80 to 120° C.

The reaction in process stage c) is preferably carried out at a pressure between 0.01 and 1000 bar, preferably 0.1 to 100 bar.

The reaction in process stage c) preferably takes place during a reaction time in the range from $1*10^{-7}$ to 1000 h.

Preferably, the alkylphosphonic acid salt (III) removed after process stage c) from the reaction mixture by filtration and/or centrifugation is dried.

Preferably, the product mixture obtained after process stage b) is reacted with the metal compounds without further purification.

Preferred solvents are the solvents mentioned in process step a).

The reaction in process stage b) and/or c) is preferably carried out in the solvent system given by stage a).

The reaction in process stage c) is preferred in a modified given solvent system. Acidic components, solubilizers, foam inhibitors, etc are added for this purpose. In a further embodiment of the method, the product mixture obtained after process stage a) and/or b) is worked up.

In a further embodiment of the method, the product mixture obtained after process stage b) is worked up and thereafter the alkylphosphonic acids and/or salts or esters (III) obtained after process stage b) are reacted in process stage c) with the metal compounds.

Preferably, the product mixture after process stage b) is worked up by isolating the alkylphosphonic acids and/or salts or esters (III) by removing the solvent system, for example by evaporation.

Preferably, the alkylphosphonic acid salt (III) of the metals Li, Na, K, Mg, Ca, Al, Ti, Zn or Fe selectively has a residual moisture content of 0.01% to 10% by weight, preferably of 0.1% to 1% by weight, an average particle size of 0.1 to 2000 μm, preferably of 10 to 500 μm, a bulk density of 80 to 800 g/l, preferably 200 to 700 g/l, and a Pfrengle flowability of 0.5 to 10, preferably of 1 to 5.

The invention more particularly provides for the use of the alkylphosphonic acid/ester/salts (III) of the present invention as acid scavengers.

When mixtures of the alkylphosphonic acid salts (III) with "classic acid scavengers" are used, the "classic acid scavengers" are preferably hydrotalcites, $C_{12}$-$C_{36}$ carboxylates, oxides, hydroxides and/or carbonates of the metals Na, Mg, Ca or Zn, for example hydrotalcite, sodium stearate, magnesium stearate, calcium stearate, zinc stearate, magnesium oxide, calcium oxide, zinc oxide or calcium carbonate.

Mixtures of the alkylphosphonic acid salts (III) with "classic acid scavengers" are used in a ratio of 5-95% by weight of alkylphosphonic acid salts (III) and 95-5% by weight of "classic acid scavengers", preferably 20-80% by weight of alkylphosphonic acid salts (III) and 80-20% by weight of "classic acid scavengers", more preferably 30-70% by weight of alkylphosphonic acid salts (III) and 70-30% by weight of "classic acid scavengers" and more preferably 40-60% by weight of alkylphosphonic acid salts (III) and 60-40% by weight of "classic acid scavengers".

Alkylphosphonic acid salts (III) and mixtures of alkylphosphonic acid salts (III) with "classic acid scavengers" are added to the polymer in a ratio of 0.0001% to 5% by weight, preferably 0.01% to 2% by weight, more preferably 0.025% to 1% by weight and even more preferably 0.05% to 0.5% by weight based on the particular polymer.

The alkylphosphonic acid salts (III) and mixtures of the alkylphosphonic acid salts (III) with "classic acid scavengers" are preferably added to the polymer at the end of the manufacturing operation, in the course of processing and further processing, in the course of the manufacture of molded articles and molding materials.

The alkylphosphonic acid salts (III) and mixtures of the alkylphosphonic acid salts (III) with "classic acid scavengers" are preferably used as powders, pellets, compactates or extrudates in solid, liquid, molten, dissolved or dispersed form optionally with other additives, for example antioxidants, antistats, blowing agents, further flame retardants, heat stabilizers, impact modifiers, processing aids, lubricants, light stabilizers, antidripping agents, compatibilizers, reinforcing agents, fillers, seed-forming agents, nucleating agents, additives for laser marking, hydrolysis stabilizers, chain extenders, color pigments, softeners, plasticizers and/or plasticizing agents and solvents.

The alkylphosphonic acid salts (III) of the present invention prove to be efficient acid scavengers for polymers coupled with simultaneously improved processing properties on the part of the polymer in respect of homogeneity and no signs whatsoever of efflorescence, spottiness, stripiness or streakiness. Moreover, the formation of deposits on die and rolling tools is minimized.

The invention further provides for the use of the alkylphosphonic acid/ester/salts (III) of the present invention as flame retardants or as intermediate stage in the manufacture of flame retardants for polymers.

The thermoplastic or thermoset molded articles and materials, films, threads and fibers made flame-retardant by alkylphosphonic acid/esters/salts (III) preferably contain from 5% to 30% by weight of the alkylphosphonic acid/ester/salts (III) produced according to one or more of claims 1 to 10, from 5% to 80% by weight of polymer or mixtures thereof, from 5% to 40% by weight of additives and from 5% to 40% by weight of filler, wherein the sum total of the components is always 100% by weight.

Preference is given to a flame retardant containing 0.1% to 90% by weight of the alkylphosphonic acid/ester/salt (III) and 0.1% to 50% by weight of further additives.

The additives preferably comprise antioxidants, antistats, blowing agents, further flame retardants, heat stabilizers, impact modifiers, processing aids, lubricants, light stabilizers, antidripping agents, compatibilizers, reinforcing agents, fillers, seed-forming agents, nucleating agents, additives for laser marking, hydrolysis stabilizers, chain extenders, color pigments, softeners, plasticizers and/or plasticizing agents.

Preferred additives are also aluminum trihydrate, antimony oxide, brominated aromatic or cycloaliphatic hydrocarbons, phenols, ethers, chloroparaffin, hexachlorocyclopentadiene adducts, red phosphorus, melamine derivatives, melamine cyanurates, ammonium polyphosphates and magnesium hydroxide. Preferred additives are also further flame retardants, more particularly salts of dialkylphosphinic acids.

Examples of preferred polymers are:

1. Polymers of mono- and diolefins (e.g., ethylene, propylene, isobutylene, butene, 4-methylpentene, isoprene, butadiene, styrene), e.g., polypropylene, polyisobutylene, polybut-1-ene, poly-4-methylpent-1-ene, polystyrene, poly(p-methylstyrene) and/or poly(alpha-methylstyrene), polyisoprene or polybutadiene, and polyethylene (optionally crosslinked), e.g., high density polyethylene (HDPE), high density and high molecular weight polyethylene (HDPE-HMW), high density and ultra high molecular weight polyethylene (HDPE-UHMW), medium density polyethylene (HMDPE), low density polyethylene (LDPE), linear low density polyethylene (LLDPE), very low density polyethylene (VLDPE), branched low density polyethylene (BLDPE), also polymers of cycloolefins, for example of cyclopentene or norbornene.

2. Blends of the polymers listed under 1., for example polypropylene with polyisobutylene, polyethylene with polyisobutylene, polypropylene with polyethylene (e.g., PP/HDPE/LDPE) and mixtures of various polyethylene types (e.g., LDPE/HDPE).

3. Copolymers of mono- and diolefins with each other and of mono- and diolefins with other vinylic monomers, for example, ethylene-propylene copolymers; LLDPE, VLDPE and blends thereof with LDPE; propylene-but-1-ene copolymers, propylene-isobutylene copolymers, ethylene-but-1-ene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers, copolymers of styrene or alpha-methylstyrene with dienes or acrylic derivatives, for example styrene-butadiene, styrene-acrylonitrile, styrene-alkyl methacrylate, styrene-butadiene-alkyl acrylate and styrene-butadiene-alkyl methacrylate, styrene-maleic anhydride, styrene-acrylonitrile-methyl acrylate; mixtures of high impact strength from styrene copolymers and another polymer, for example a polyacrylate, a diene polymer or an ethylene-propylene-diene terpolymer; also block copolymers of styrene, for example styrene-butadiene-styrene, styrene-isoprene-styrene, styrene-ethylene/butylene-styrene or styrene-ethylene/propylene-styrene, and also graft copolymers of styrene or alpha-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on poly(alkyl acrylate)s or poly(alkyl methacrylate)s, styrene and acrylonitrile on acrylate-butadiene copolymers, and also their mixtures, as are also known for example as ABS, MBS, ASA or AES polymers; also their copolymers with carbon monoxide or ethylene-acrylic acid copolymers and their salts (ionomers) and also terpolymers of ethylene with propylene and a diene such as, for example, hexadiene, dicyclopentadiene or ethylidenenorbornene; and blends of such copolymers with each other and/or polymers mentioned under 1., for example polypropylene-ethylene-propylene copolymer, LDPE-ethylene-vinyl acetate copolymer, LDPE-ethylene-acrylic acid copolymer, LLDPE-ethylene-vinyl acetate copolymer, LLDPE-ethylene-acrylic acid copolymer, and alternating or random polyalkylene-carbon monoxide copolymers and blends thereof with other polymers, such as polyamides for example.

4. Polymers of unsaturated alcohols or amines or the acyl derivatives or acetals thereof, for example polyvinyl alcohols, polyvinyl acetates, polyvinyl stearates, polyvinyl benzoates, polyvinyl maleates, polyvinyl butyrates, polyallyl phthalates or polyallylmelamines; and also their copolymers with olefins mentioned under 1.

5. Polyacetals such as, for example, polyoxymethylene and such polyoxymethylenes as contain comonomers, for example ethylene oxides; also polyacetals modified with thermoplastic polyurethanes, acrylates or MBS.

6. Polyphenylene oxides and sulfides, and blends thereof with styrene polymers or polyamides.

7. Polyamides and copolyamides derived from diamines and dicarboxylic acids and/or from aminocarboxylic acids or the corresponding lactams, such as nylon-2,12, nylon-4, nylon-4,6, nylon-6, nylon-6,6, nylon-6,9, nylon-6,10, nylon-6,12, nylon-6,66, nylon-7,7, nylon-8,8, nylon-9,9, nylon-10,9, nylon-10,10, nylon-11, nylon-12; aromatic polyamides proceeding from m-xylene, diamine and adipic acid; polyamides produced from hexamethylenediamine and iso- and/or terephthalic acid and optionally an elastomer as modifier, for example poly-2,4,4-trimethylhexamethyleneterephthalamide or poly-m-phenyleneisophthalamide, block copolymers of the aforementioned polyamides with polyolefins, olefin copolymers, ionomers or chemically bonded or grafted elastomers or with polyethers, for example with polyethylene glycol, polypropylene glycol or polytetramethylene glycol. Also EPDM- or ABS-modified polyamides or copolyamides; and also polyamides condensed during processing ("RIM polyamide systems").

8. Polyurea, polyimides, polyamide imides, polyether imides, polyester amides, polyhydantoins and polybenzimidazoles.

9. Polyesters derived from dicarboxylic acids and their esters and diols and/or from hydroxy carboxylic acids, preferably terephthalic acid and ethylene glycol, 1,3-propanediol and 1,3-butanediol, or the corresponding lactones, for example polyethylene terephthalate, polybutylene terephthalate, poly-1,4-dimethylolcyclo-hexane terephthalate, polyhydroxybenzoates, and also block polyether esters derived from polyethers having hydroxyl end groups; further polyesters modified with polycarbonates or MBS.

10. Polycarbonates and polyester carbonates.

11. Polysulfones, polyether sulfones and polyether ketones.

12. Crosslinked polymers derived from aldehydes with phenols, urea or melamines, for example phenol-formaldehyde resin, urea-formaldehyde resin and melamines-formaldehyde resin.

13. Alkyd resins.

14. Unsaturated polyester resins derived from copolyesters of saturated or unsaturated dicarboxylic acids with polyhydric alcohols and vinylic compounds as crosslinking agents.

15. Blends of the aforementioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PU, PC/thermoplastic PU, POM/acrylates, POM/MBS, PPO/MBS, PPO/HIPS, PPO/PA 6.6 and, copolymers, PA/HDPE, PA/PP, PA/PPO, PBT/ABS or PBT/PET/PC.

16. Natural and synthetic organic substances forming pure monomers or blends thereof, for example mineral oil, animal or vegetable fats, oils and waxes, waxes and fats based on synthetic esters (for example phthalates, adipates, phosphates or trimellitates), and also blends of synthetic esters with mineral oils in any desired composition.

The examples which follow illustrate the invention.

Production, processing and testing of flame-retardant polymeric molding materials and flame-retardant polymeric molded articles.

The flame-retardant components are mixed with the polymeric pellets and any additives and incorporated on a twin-screw extruder (Leistritz LSM® 30/34) at temperatures of 230 to 260° C. (glassfiber-reinforced PBT) or of 260 to 280° C. (glassfiber-reinforced PA 66). The homogenized polymeric strand was hauled off, water bath cooled and then pelletized.

After sufficient drying, the molding materials were processed on an injection molding machine (Aarburg Allrounder) at melt temperatures of 240 to 270° C. (glassfiber-reinforced PBT) or of 260 to 290° C. (glassfiber-reinforced PA 66) to give test specimens. The test specimens are subsequently flammability tested and classified using the UL 94 (Underwriter Laboratories) test.

UL 94 (Underwriter Laboratories) fire classification was determined on test specimens from each mixture, using test specimens 1.5 mm in thickness.

The UL 94 fire classifications are as follows:

V-0 afterflame time never longer than 10 sec, total of afterflame times for 10 flame applications not more than 50 sec, no flaming drops, no complete consumption of the specimen, afterglow time for specimens never longer than 30 sec after end of flame application.

V-1 afterflame time never longer than 30 sec after end of flame application, total of afterflame time for 10 flame applications not more than 250 sec, afterglow time for specimens never longer than 60 sec after end of flame application, other criteria as for V-0

V-2 cotton indicator ignited by flaming drops, other criteria as for V-1 not classifiable (ncl) does not comply with fire classification V-2.

Chemicals and abbreviations used

VE water completely ion-free water

AIBN azobis(isobutyronitrile), (from WAKO Chemicals GmbH)

WakoV65 2,2'-azobis(2,4-dimethylvaleronitrile), (from WAKO Chemicals GmbH)

Deloxan® THP II metal scavenger (from Evonik Industries AG)

EXAMPLE 1

At room temperature, a three-neck flask equipped with stirrer and high-performance condenser is initially charged with 188 g of water and this initial charge is devolatilized by stirring and passing nitrogen through it. Then, under nitrogen, 0.2 mg of palladium(II) sulfate and 2.3 mg of tris(3-sulfophenyl)phosphine trisodium salt are added, the mixture is stirred, and then 66 g of phosphinic acid in 66 g of water are added. The reaction solution is transferred to a 2 l Büchi reactor and charged with ethylene under superatmospheric pressure while stirring and the reaction mixture is heated to 80° C. After 28 g of ethylene has been taken up, the system is cooled down and free ethylene is discharged. The reaction mixture is freed of solvent on a rotary evaporator. The residue is admixed with 100 g of VE water and at room temperature stirred under nitrogen, then filtered and the filtrate is extracted with toluene, thereafter freed of solvent on a rotary evaporator and the resulting ethylphosphonous acid is collected. 92 g (98% of theory) of ethylphosphonous acid are obtained.

EXAMPLE 2

Example 1 is repeated with 99 g of phosphinic acid, 63 g of propene, 6.9 mg of tris(dibenzylideneacetone)dipalladium and 9.5 mg of 4,5-bis(diphenylphosphino)-9,9-dimethylxanthene in 400 g of tetrahydrofuran to obtain 157 g (97% of theory) of propylphosphonous acid.

EXAMPLE 3

Example 1 is repeated with 99 g of phosphinic acid, 84 g of butene, 8.7 mg of bis(dibenzylideneacetone)palladium and 9.1 mg of 1,1'-bis(diphenylphosphino)-ferrocene in 400 g of butanol to obtain 173 g (96% of theory) of butylphosphonous acid.

EXAMPLE 4

Example 1 is repeated with 99 g of phosphinic acid, 156 g of styrene, 8.7 mg of bis(dibenzylideneacetone)palladium and 5.7 mg of 4,6-bis(diphenylphosphino)-phenoxazine in 400 g of acetonitrile to obtain 240 g (94% of theory) of 2-phenyl-ethylphosphonous acid.

EXAMPLE 5

Example 1 is repeated with 99 g of phosphinic acid, 84 g of i-butene, 8.7 mg of bis(dibenzylideneacetone)palladium and 9.5 mg of 4,5-bis(diphenylphosphino)-9,9-dimethylxanthene in 400 g of butanol to obtain 151 g (84% of theory) of i-butylphosphonous acid.

EXAMPLE 6

99 g (0.75 mol) of phosphinic acid, 86 g (0.76 mol) of octene, 34 mg of tris(dibenzylideneacetone)dipalladium and 48 mg of 4,5-bis(diphenylphosphino)-9,9-dimethylxanthene in 750 g of tetrahydrofuran are reacted at about 70° C. for 9 hours, passed through a column charged with Deloxan® THP II for purification and freed of solvent in a rotary evaporator. The residue is admixed with 500 g of completely ion-free water and stirred, and then filtered, the filtrate is extracted with ethyl acetate. This is followed by removal of solvent in a rotary evaporator to obtain 117 g (84% of theory) of octylphosphonous acid.

EXAMPLE 7

Example 6 is repeated with 66 g (0.5 mol) of phosphinic acid, 114.5 g (0.5 mol) of hexadecene, 23 mg of tris(dibenzylideneacetone)dipalladium and 32 mg of 4,5-bis(diphenylphosphino)-9,9-dimethylxanthene in 500 g of tetrahydrofuran, passed through a column charged with Deloxan® THP II for purification and freed of solvent in a rotary evaporator. The residue is admixed with 500 g of completely ion-free water and stirred, and then filtered and the residue is washed with cold water and acetone to obtain 127 g (81% of theory) of hexadecylphosphonous acid.

EXAMPLE 8

Example 7 is repeated with 66 g (0.5 mol) of phosphinic acid, 140.0 g (0.5 mol) of octadecene, 23 mg of tris(dibenzylideneacetone)dipalladium and 32 mg of 4,5-bis(diphenylphosphino)-9,9-dimethylxanthene in 500 g of tetrahydrofuran followed by working up to obtain 157 g (85% of theory) of octadecylphosphonous acid.

EXAMPLE 9

Example 1 is repeated with 99 g of phosphinic acid, 396 g of butanol, 42 g of ethylene, 6.9 mg of tris(dibenzylideneacetone)dipalladium and 9.5 mg of 4,5-bis-(diphenylphosphino)-9,9-dimethylxanthene, followed by purification over a column charged with Deloxan® THP II and the further addition of n-butanol. At a reaction temperature of 80-110° C., the water formed is removed by azeotropic distillation. The product (butyl ethylphosphonite) is purified by distillation at reduced pressure. Yield: 189 g (84% of theory).

EXAMPLE 10

Example 1 is repeated with 198 g of phosphinic acid, 198 g of water, 84 g of ethylene, 6.1 mg of palladium(II) sulfate and 25.8 mg of 9,9-dimethyl-4,5-bis-(diphenylphosphino)-2,7-sulfonatoxanthene disodium salt, followed by purification over a column charged with Deloxan® THP II and the further addition of n-butanol. At a reaction temperature of 80-110° C., the water formed is removed by azeotropic distillation. The product (butyl ethylphosphonite) is purified by distillation at reduced pressure. Yield: 374 g (83% of theory).

EXAMPLE 11

A 500 ml five-neck flask equipped with gas inlet tube, thermometer, high-performance stirrer and reflux condenser with gas incineration is charged with 94 g (1 mol) of ethylphosphonous acid (produced as in Example 1). Ethylene oxide is introduced at room temperature. A reaction temperature of 70° C. is set with cooling, followed by further reaction at 80° C. for one hour. The ethylene oxide takeup is 65.7 g. The acid number of the product is less than 1 mg KOH/g. 129 g (94% of theory) of 2-hydroxyethyl ethylphosphonite are obtained as colorless, water-clear product.

EXAMPLE 12

9.4 g (0.1 mol) of ethylphosphonous acid (produced as in example 1) are dissolved in 150 ml of water and adjusted to pH 9 with 2N NaOH solution. This is followed by the addition of 0.45 g of charcoal comprising 5% Pt and 1% Bi, heating of the suspension to 70° C. and passing air (10 l/h) through the suspension. All the while, the pH of the suspension is maintained at pH=9 by addition of 2N NaOH solution. After the reaction has ended, the reaction solution is filtered to remove the catalyst, washed, acidified with hydrochloric acid and the water is distilled off under reduced pressure. The residue is taken up in tetrahydrofuran and extracted. The insoluble salts are filtered off to obtain 10.7 g (97% of theory) of ethylphosphonic acid as a colorless solid.

EXAMPLE 13

29.0 g (0.1 mol) of hexadecylphosphonous acid (produced as in example 7) are suspended in 150 ml of water and at about 30° C. 30% strength hydrogen peroxide solution is passed through the suspension at a flow rate of 1 mol equivalent per hour. After the reaction has ended after 6 hours, the reaction solution is filtered and the residue is dried under reduced pressure to obtain 29.7 g (97% of theory) of hexadecylphosphonic acid as a colorless solid.

EXAMPLE 14

15.0 g (0.1 mol) of i-butylphosphonous acid (produced as in example 5) in 500 ml of acetone are dropwise admixed with 0.11 mol of Jones reagent (12.7 g of chromium trioxide in 36.7 ml of water and 11.0 ml of concentrated sulfuric acid) at 0° C. The reaction mixture is additionally stirred for 3½ hours with ice cooling and 1 hour at room temperature. After 12 ml of isopropanol had been added, the mixture is poured onto ice-water. Volatile constituents are subsequently distilled off under reduced pressure. The residue is taken up in tetrahydrofuran and extracted. Insoluble salts are filtered off and the solvent of the filtrate is removed under reduced pressure. Following chromatographic purification, 13.8 g (83% of theory) of i-butylphosphonic acid are obtained as an oil.

EXAMPLE 15

20.6 g (0.1 mol) of octylphosphonous acid (produced as in example 6) and 8 g (0.2 mol) of sodium hydroxide are suspended in 250 ml of water and admixed with 23.7 g (0.15 mol) of potassium permanganate added a little at a time with vigorous stirring. The reaction temperature throughout the entire reaction is kept below 15° C. by cooling with ice-water. The reaction mixture is stirred and, following a reaction time of 5 hours, admixed with 12 ml of isopropanol. Manganese oxide formed is filtered, the filtrate acidified with dilute hydrochloric acid and thereafter volatile constituents are distilled off under reduced pressure. The residue is taken up in tetrahydrofuran and extracted. Insoluble salts are filtered off and the solvent of the filtrate is removed under reduced pressure to leave 20.7 g (94% of theory) of octylphosphonic acid.

EXAMPLE 16

An aqueous solution of 220 g (2 mol) of ethylphosphonic acid (produced as in example 12) is reacted with about 160 g of a 50% strength aqueous solution of sodium hydroxide and the water is distilled off under reduced pressure to obtain 302 g (98% of theory) of ethylphosphonic acid disodium salt as a colorless solid.

EXAMPLE 17

306 g (1 mol) of hexadecylphosphonic acid (produced as in example 13) are suspended in 1.5 l of hexane and 200 ml of a 10 molar solution of sodium hydroxide are added; the suspension is refluxed for 2 hours and water removed by azeotropic distillation. The reaction solution is filtered and the residue is washed with water and hexane and dried under reduced pressure to obtain 340 g (97% of theory) of hexadecylphosphonic acid disodium salt as a colorless solid.

EXAMPLE 18

Example 17 is repeated with 306 g (1 mol) of hexadecylphosphonic acid (produced as in example 13) and 100 ml of a 10 molar solution of sodium hydroxide being reacted in 1.5 l of hexane to obtain 320 g (98% of theory) of hexadecylphosphonic acid monosodium salt as colorless solid.

EXAMPLE 19

306 g (1 mol) of hexadecylphosphonic acid (produced as in example 13) are suspended in 1.5 l of hexane and 200 ml of a 10 molar solution of sodium hydroxide are added and the suspension is refluxed for 2 hours. Then, 500 ml of a 1 molar solution of calcium chloride are added, and the suspension is refluxed for 4 hours and water removed by azeotropic distillation. The reaction solution is filtered and the residue is washed with water and hexane and dried under reduced pressure to obtain 313 g (96% of theory) of hexadecylphosphonic acid calcium salt as colorless solid.

EXAMPLE 20

660 g (6 mol) of ethylphosphonic acid (produced as in Example 12) are dissolved in 860 g of water and initially charged into a 5 l five-neck flask equipped with thermometer, reflux condenser, high-performance stirrer and dropping funnel and neutralized with about 960 g (12 mol) of 50% sodium hydroxide solution. A mixture of 2583 g of a 46% aqueous solution of $Al_2(SO_4)_3 \cdot 14 \, H_2O$ is added at 85° C. The solid material obtained is subsequently filtered off, washed with hot water and dried at 130° C. in vacuo. Yield: 718 g (95% of theory) of ethylphosphonic acid aluminum(III) salt as colorless salt.

EXAMPLE 21

165 g (1.5 mol) of ethylphosphonic acid (produced as in Example 12) are at 85° C. dissolved in 400 ml of toluene and admixed with 444 g (6 mol) of butanol. At a reaction temperature of about 100° C., the water formed is removed by azeotropic distillation. 296 g (89% of theory) of butyl ethylphosphonate are obtained by distillation at reduced pressure.

EXAMPLE 22

Hexadecylphosphonic acid mono- and disodium salts (acid scavengers) are added in the concentrations reported in the table below to an LLDPE melt (obtained by Ziegler-Natta polymerization) as a suspension in isopar. The polymer obtained was extruded and pelletized. To demonstrate the efficacy of the acid scavengers, the HCl concentration in the effluent gas of the LLDPE manufacturing process was determined by means of Drager-Rohrchen tubelet, the acidity of the polymer is determined by alkalimetric titration of the ground polymer, and the corrosivity of the polymer is determined on steel plates by determining the corrosion index.

| Product | Acid scavenger concentration [% by wt.] | HCL in effluent gas [ppm] | Acidity of polymer [ppm HCl] | Corrosion index |
|---|---|---|---|---|
| Hexadecylphosphonic acid disodium salt, ex. 17 | 0.05 | 19 | 0.05 | 0 |
| Hexadecylphosphonic acid disodium salt, ex. 17 | 0.10 | 3.5 | 0.05 | 0.03 |
| Hexadecylphosphonic acid monosodium salt, ex. 18 | 0.10 | 1.8 | 0.01 | 0 |
| Hexadecylphosphonic acid calcium salt, ex. 19 | 0.10 | 4.5 | 0.05 | 0.06 |
| Calcium stearate | 0.10 | 32 | 0.2 | 0.3 |

The results in respect of the HCl concentration in the effluent gas as well as in the polymer provide clear evidence that the inventive hexadecylphosphonic acid sodium salts have significantly better neutralization properties compared with the "classic acid scavenger" calcium stearate. Illustrated by the lower corrosion indices, moreover, apparatus is treated distinctly more benignly than in the prior art.

EXAMPLE 23

A mixture of 50% by weight of polybutylene terephthalate, 20% by weight of ethylphosphonic acid aluminum(III) salt (produced as in Example 20) and 30% by weight of glass fibers are compounded on a twin-screw extruder (Leistritz LSM 30/34) at temperatures of 230 to 260° C. to form a polymeric molding material. The homogenized polymeric strand was hauled off, water bath cooled and then pelletized.

After drying, the molding materials are processed on an injection molding machine (Aarburg Allrounder) at 240 to 270° C. to form polymeric molded articles which achieved a UL-94 classification of V-1.

What is claimed is:

1. A method for producing alkylphosphonic acids, esters or salts, comprising the steps of:

a) reacting a phosphinic acid source (I)

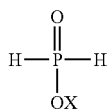

(I)

with olefins (IV)

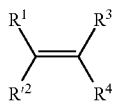

(IV)

in the presence of a catalyst A to form an alkylphosphonous acid, salt or ester (II)

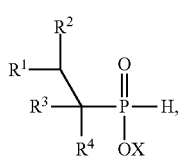

(II)

b) reacting the alkylphosphonous acid, salt or ester (II) with at least one oxidant or with at least one oxidant and water or in the presence of a catalyst B with oxygen and water to form an alkylphosphonic acid derivative (III)

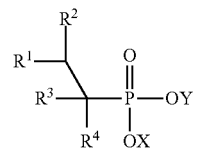

(III)

wherein $R^1$, $R^2$, $R^3$, $R^4$ are identical or different and are H, methyl, ethyl, n propyl, isopropyl, n-butyl, isobutyl, tert-butyl, phenyl or a combination thereof and X and Y are identical or different and are H, methyl, ethyl, n propyl, isopropyl, n-butyl, isobutyl, tert-butyl, phenyl, ethylene glycol, propyl glycol, butyl glycol, pentyl glycol, hexyl glycol, allyl and/or glycerol Mg, Ca, Al, Sb, Sn, Ge, Ti, Fe, Zr, Zn, Ce, Bi, Sr, Mn, Cu, Ni, Li, Na, K a protonated nitrogen base or a combination thereof and the catalysts A and B are transition metals, transition metal compounds, catalyst systems composed of a transition metal, transition metal compound and at least one ligand or a combination thereof and wherein the oxidizing agents are selected from the group of potassium permanganate, manganese oxide, chromium trioxide, potassium dichromate, pyridine dichromate, pyridine chlorochromate, Collins reagent, Jones reagent, Corey-Gilman-Ganem reagent, (Dess-Martin)periodinane, periodoxybenzoic acid, ruthenium tetroxide, ruthenium dioxide, tetra-n-propyl perruthenate, ruthenium trichloride/sodium periodate, ruthenium dioxide/sodium periodate, chlorine, hypochlorite, peracids, peroxo compounds or a combination thereof and wherein the transition metals and transition metal compounds are rhodium, nickel, palladium, platinum, ruthenium, gold or a combination thereof.

2. The method according to claim 1 wherein the alkylphosphonic acid, its salt or ester (III) obtained after step b) is subsequently reacted in a step c) with metal compounds of Mg, Ca, Al, Sb, Sn, Ge, Ti, Fe, Zr, Zn, Ce, Bi, Sr, Mn a protonated nitrogen base or a combination thereof to form the alkylphosphonic acid salts (III) of these metals, of a nitrogen compound or a combination thereof.

3. The method according to claim 2 wherein the alkylphosphonous acid, salt or ester (II) obtained after step a), the alkylphosphonic acid, salt or ester (III) obtained after step b), the resulting reaction solution thereof or a combination thereof are esterified with an alkylene oxide or an alcohol M-OH, M'-OH or a combination thereof wherein the alcohol of the general formula M-OH comprises linear or branched, saturated and unsaturated, monohydric organic alcohols having a carbon chain length of C1-C18 and the alcohol of the general formula M' OH comprises linear or branched, saturated and unsaturated polyhydric organic alcohols having a carbon chain length of C1-C18, and the resulting alkylphosphonous ester (II), alkylphosphonic ester (III) or combination thereof are subjected to the further reaction steps b) or c).

4. The method according to claim 1, wherein X and Y are identical or different and are H, Li, Na, K, Ca, Mg, Al, Zn, Ti or Fe.

* * * * *